United States Patent
Jewell

(10) Patent No.: US 10,130,603 B2
(45) Date of Patent: Nov. 20, 2018

(54) METHODS AND COMPOSITIONS FOR IMPROVING KIDNEY FUNCTION

(71) Applicant: Hill's Pet Nutrition, Inc., Topeka, KS (US)

(72) Inventor: Dennis Jewell, Lawrence, KS (US)

(73) Assignee: Colgate-Palmolive Company, New York, NY (US)

( * ) Notice: Subject to any disclaimer, the term of this patent is extended or adjusted under 35 U.S.C. 154(b) by 12 days.

(21) Appl. No.: 15/034,364

(22) PCT Filed: Nov. 5, 2013

(86) PCT No.: PCT/US2013/068455
§ 371 (c)(1),
(2) Date: May 4, 2016

(87) PCT Pub. No.: WO2015/069215
PCT Pub. Date: May 14, 2015

(65) Prior Publication Data
US 2016/0287543 A1   Oct. 6, 2016

(51) Int. Cl.
*A61K 31/205* (2006.01)
*A61P 13/12* (2006.01)
*A61K 31/202* (2006.01)

(52) U.S. Cl.
CPC .......... *A61K 31/205* (2013.01); *A61K 31/202* (2013.01); *A61P 13/12* (2018.01)

(58) Field of Classification Search
CPC ...... A61K 31/202; A61K 31/205; A61P 13/12
See application file for complete search history.

(56) References Cited

U.S. PATENT DOCUMENTS

| | | | |
|---|---|---|---|
| 5,728,678 A | 3/1998 | Trimbo et al. | |
| 5,753,703 A | 5/1998 | Cavazza et al. | |
| 7,867,948 B2 | 1/2011 | Gastner et al. | |
| 8,492,432 B2 | 7/2013 | Zicker et al. | |
| 8,859,613 B2 | 10/2014 | Zicker et al. | |
| 9,149,062 B2 * | 10/2015 | Friesen | A23L 1/304 |
| 9,173,427 B2 * | 11/2015 | Friesen | A23L 1/304 |
| 2003/0013767 A1 | 1/2003 | Bessman | |
| 2005/0192352 A1 * | 9/2005 | Caterson | A61K 31/202 514/560 |
| 2008/0206398 A1 * | 8/2008 | Yamka | A01K 5/00 426/2 |
| 2011/0288012 A1 | 11/2011 | Somekawa et al. | |
| 2012/0172330 A1 | 7/2012 | Buck et al. | |

FOREIGN PATENT DOCUMENTS

| | | |
|---|---|---|
| CN | 101480230 A | 7/2009 |
| JP | 2012-019691 A | 2/2012 |
| RU | 2400251 | 9/2010 |
| WO | 1996034846 | 11/1996 |
| WO | WO 00/067690 | 11/2000 |
| WO | 2002002105 | 1/2002 |
| WO | 2002096408 | 12/2002 |
| WO | WO 04/075653 | 9/2004 |
| WO | 2005032591 | 4/2005 |
| WO | WO 2006/020768 | 2/2006 |
| WO | WO 07/022344 | 2/2007 |
| WO | WO 2009/055933 | 5/2009 |
| WO | WO 2010/064714 | 6/2010 |
| WO | WO 2011/087769 | 7/2011 |
| WO | WO 2013/101367 | 7/2013 |
| WO | WO 2013/153071 | 10/2013 |

OTHER PUBLICATIONS

Bezard et al., J. Am. Oil Chem. Soc. 48, 134-39 (1971).*
Hall et al., 2012, "Feeding Healthy Beagles Medium-Chain Triglycerides, Fish Oil, and Carnitine Offsets Age-Related Changes in Serum Fatty Acids and Carnitine Metabolites," PLOS ONE 7(11):e49510.
Kanazawa, et al., 2013, "Favorable effects of a newly developed liquid diet for patients with renal failure on a low protein diet," Clinical Nutrition 32(Suppl.1):S72, Abstract No. PP132-SUN.
Gualano et al., 2008, "Effects of creatine supplementation on renal function: a randomized, double-blind, placebo-controlled clinical trial," Eur. J Appl. Physiol. 103(1):33-40.
International Search Report and Written Opinion in International Application No. PCT/US2013/068455 dated Dec. 13, 2013.
MedlinePlus Supplements, 1995, "Fish oil," http://www.nlm.nih.gov/medlineplus/druginfo/natural/993.html; accessed 2013, pp. 1-10.
Sener et al., 2004, "L-Carnitine Ameliorates Oxidative Damage due to Chronic Renal Failure in Rats", Journal of Cardiovascular Pharmacology 43(5):698-705.
Song, et al. 2004, "Effects of dietary fat, NaCl, and fructose on renal sodium and water transporter abundances and systemic blood pressure," Am J Physiol. Renal Physiol. 287:F1204-F1212.
Tan et al., 2009, "Garouper hepatinica as feed additive for preventing fatty infiltration to liver of garouper, prepared from vitamin F, sinkaline, L-carnitine, lecithin, selenium methiorline, eicosapentanoic acid and docosahexanoic acid," Thomson WPI Database Accession No. 2009-L85513, CN20081219368.
Yoshizumi et al., 2004, "Effects of creatine supplementation on renal function", J Herb Pharmacother. 4(1):1-7.

* cited by examiner

*Primary Examiner* — Theodore R. West

(57) ABSTRACT

Provided are methods and compositions for improving kidney function and for the treatment or prophylaxis of kidney disease in dogs.

26 Claims, No Drawings

METHODS AND COMPOSITIONS FOR IMPROVING KIDNEY FUNCTION

BACKGROUND

The kidneys filter waste products from the body (e.g., urea and creatinine), regulate electrolytes (e.g., sodium, potassium, and chloride), produce hormones that help control red blood cell production and blood pressure, produce and concentrate urine, and maintain proper hydration. Once kidney damage occurs, the consequences are usually irreversible.

One estimate provides that 9 in every 1,000 dogs suffer from kidney disease. Kidney disease may occur in dogs of all ages, but is usually a disease of older pets. For kidney disease dogs with chronic renal failure, the mean age of diagnosis is 7 years.

Dietary therapy may help manage kidney failure in dogs. However, despite years of studies and developments relating to kidney disease and renal function, kidney disease and poor renal function remain a major health problem for dogs. There is, therefore, a need for new methods and compositions for preventing and treating kidney disease and for improving kidney function in dogs.

BRIEF SUMMARY

It has been surprisingly discovered that administering a composition comprising an effective amount of L-carnitine, eicosapentaenoic acid, and docosahexaenoic acid may improve kidney function and may be used for the treatment or prophylaxis of kidney disease.

Provided are methods for improving kidney function in a dog in need thereof.

Also provided are methods for the treatment or prophylaxis of kidney disease in a dog in need thereof.

Also provided are compositions for improving kidney function in a dog in need thereof.

Also provided are compositions for the treatment or prophylaxis of kidney disease in a dog in need thereof.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

DETAILED DESCRIPTION

The following description of the preferred embodiment(s) is merely exemplary in nature and is in no way intended to limit the invention, its application, or uses.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. All percentages expressed herein are on a weight by dry matter basis unless specifically stated otherwise.

As used herein, "treating" or "treatment" means reversing, alleviating, mitigating or inhibiting the progress of the disorder or condition to which such term applies, or one or more symptoms of such disorder or condition.

As used herein, the singular forms "a", "an", and "the" include plural reference unless the context clearly dictates otherwise.

As used herein, "animal" refers to any animal, e.g., avian, bovine, dog, equine, feline, hicrine, murine, ovine, or porcine. In some embodiments, the animal is a mammal. In some embodiments, the animal is a dog or feline.

As used herein, "renal drug" refers to any compound, composition, or drug useful for the treatment or prophylaxis of kidney disease.

As used herein, "L-carnitine" refers to L-carnitine in free or salt form. In some embodiments, L-carnitine in salt form refers to an L-carnitine salt that is safe to ingest by a dog.

As used herein, "in conjunction" means that one or more of the compositions and compounds (e.g. renal drugs or composition components) of the present invention are administered to an animal (1) together in a composition according to this disclosure or (2) separately at the same or different frequency using the same or different administration routes at about the same time or periodically.

As used herein, "improve kidney function" or "improving kidney function" means that a composition is administered to or a method is used for an animal for a period effective to improve kidney function as determined by comparison with kidney function in animals not being administered the composition or using the method.

Kidney function may be measured by any method of assessing kidney function known in the art. For example, kidney function may be assessed by determining glomerular filtration rate and/or measuring the level(s) of one or more biomarkers in a tissue or biofluid sample, e.g., creatinine and/or symmetrical dimethyl arginine (SDMA).

As used herein, "dog" includes those dogs which are companion animals such as Canis familiaris, working dogs and the like. The term dog is synonymous with the term canine.

As used herein, "dog food" refers to a composition intended for ingestion by a dog and formulated as nutritionally balanced compositions suitable for daily feed.

As used herein, "an amount effective" or "an effective amount" refers to that amount of a compound, material, or composition as described herein that may be effective to achieve a particular biological result, e.g., to improve kidney function or for the treatment or prophylaxis of kidney disease. In one embodiment, compositions of the present invention, e.g., Composition 1, e.g., 1.1-1.176 (vida infra) or, e.g., Composition 2, e.g., 2.1-2.176 (vida infra) are dog food. A nutritionally balanced composition provides sufficient nutrients for maintenance of normal health of a healthy dog.

As used herein, "medium chain fatty acid" refers to a fatty acid having from 6 to 14 carbon atoms, e.g., a saturated medium chain fatty acid, e.g., caproic acid, caprylic acid, capric acid, lauric acid, or myristic acid, e.g., capric acid, lauric acid, or myristic acid.

As used herein, "medium chain triglyceride oil" refers to an oil that comprises more medium chain triglycerides than long and/or short chain triglycerides, e.g., coconut oil.

A nutritionally balanced composition is palatable and, together with water, provides the sole source of all of the nutrition necessary for maintenance of normal health in a healthy dog. Nutritionally balanced compositions are familiar to one of skill in the art. For example, nutrients and ingredients such as those disclosed herein as well as others suitable for animal feed compositions, and recommended amounts thereof, may be found, for example, in the 2012 Official Publication of the Associate of American Feed Control Officials ("AAFCO"), Inc., or in the National Research Council Animal Nutrition Series Nutrient Requirements of Dogs and Cats, 2006. For example, dog food may contain protein, fat, carbohydrate, dietary fiber, amino acids, minerals, vitamins, and other ingredients in amounts known by those of skill in the art.

As used herein, "renal drug(s)" is any renal drug known to skilled artisans to be useful for combating kidney disease. A renal drug may be administered to the dog using any method appropriate for the renal drug and in amounts known to skilled artisans to be sufficient for the treat or prophylaxis of renal disease.

Protein may be supplied by any of a variety of sources known by those skilled in the art, including plant sources, animal sources, or both. Animal sources include, for example, meat, meat by-products, seafood, dairy, eggs, etc. Meats include, for example, the flesh of poultry, fish, and mammals (e.g., cattle, pigs, sheep, goats, and the like). Meat by-products include, for example, lungs, kidneys, brain, livers, and stomachs and intestines (freed of all or essentially all their contents). The protein can be intact, almost completely hydrolyzed, or partially hydrolyzed. Typical protein amounts in the composition of the invention are at least about 10% (or from about 10% to about 55%, or from about 13% to about 50%, or from about 14% to about 36%).

Fat may be supplied by any of a variety of sources known by those skilled in the art, including meat, meat by-products, fish oil, and plants. Plant fat sources include wheat, flaxseed, rye, barley, rice, sorghum, corn, oats, millet, wheat germ, corn germ, soybeans, peanuts, and cottonseed, as well as oils derived from these and other plant fat sources. The compositions of the invention typically contain at least about 4% (or from about 4% to about 50%, or from about 8% to about 25%, or from about 15% to about 22%) total fat.

Arachidonic acid ("AA") may be provided from a variety of natural sources. Liver, e.g., chicken liver, is relatively high in AA. On the other hand, fish oil is relatively high in eicosapentaenoic acid ("EPA") and docosahexaenoic acid ("DHA").

Carbohydrate may be supplied by any of a variety of sources known by those skilled in the art, including beet pulp, parboiled rice, corn starch, corn gluten meal, and any combination of those sources. Grains supplying carbohydrate include, but are not limited to, wheat, corn, barley, sorgum, and rice. Carbohydrate content of foods may be determined by any number of methods known by those of skill in the art. Generally, carbohydrate percentage may be calculated as nitrogen free extract ("NFE"), which may be calculated as follows: NFE=100%–moisture %–protein %–fat %–ash %–crude fiber %.

Dietary fiber refers to components of a plant which are resistant to digestion by an animal's digestive enzymes. Dietary fiber includes soluble and insoluble fibers. Soluble fiber are resistant to digestion and absorption in the small intestine and undergo complete or partial fermentation in the large intestine, e.g., beet pulp, guar gum, chicory root, psyllium, pectin, blueberry, cranberry, squash, apples, oats, beans, citrus, barley, or peas. Insoluble fiber may be supplied by any of a variety of sources, including oat fiber, cellulose, peanut hulls, whole wheat products, wheat oat, corn bran, flax seed, grapes, celery, green beans, cauliflower, potato skins, fruit skins, vegetable skins, peanut hulls, and soy fiber. Crude fiber includes indigestible components contained in cell walls and cell contents of plants such as grains, e.g., hulls of grains such as rice, corn, and beans. Typical fiber amounts in the composition of the invention are from about 0 to about 10%, or from about 1% to about 5%.

Amino acids, including essential amino acids, may be added to the dog food of the present invention as free amino acids, or supplied by any number of sources, e.g., intact protein, to the compositions of the present invention. Essential amino acids are amino acids that cannot be synthesized de novo, or in sufficient quantities by an organism and thus must be supplied in the diet. Essential amino acids vary from species to species, depending upon the organism's metabolism. For example, it is generally understood that the essential amino acids for dogs and cats (and humans) are phenylalanine, leucine, methionine, lysine, isoleucine, valine, threonine, tryptophan, histidine and arginine.

A dog food of the present disclosure may also contain one or more minerals and/or trace elements, e.g., calcium, phosphorus, sodium, potassium, chloride, magnesium, manganese, copper, zinc, iron, iodine, and selenium, in amounts required to avoid deficiency and maintain health. These amounts are known by those of skill in the art, for example, as provided in the 2012 Official Publication of the Associate of American Feed Control Officials, Inc. ("AAFCO"), or in the National Research Council Animal Nutrition Series Nutrient Requirements of Dogs and Cats, 2006. Typical mineral amounts are from about 0.1 to about 4% or from about 0.10% to about 2%.

A dog food of the present disclosure may also include vitamins in amounts required to avoid deficiency and maintain health. These amounts, and methods of measurement are known by those skilled in the art. For example, the 2012 Official Publication of the Associate of American Feed Control Officials, Inc. ("AAFCO"), or in the National Research Council Animal Nutrition Series Nutrient Requirements of Dogs and Cats, 2006 provides recommended amounts of such ingredients for dogs. As contemplated herein, useful vitamins may include, but are not limited to, vitamin A, vitamin $B_1$, vitamin $B_2$, vitamin $B_3$, vitamin $B_5$, vitamin $B_6$, vitamin $B_{12}$, vitamin C, vitamin D, vitamin E, vitamin H (biotin), vitamin K, folic acid, choline, inositol, niacin, and pantothenic acid. Typical vitamin amounts in the composition of the invention are from about 0 to about 3% or from about 1% to about 2%.

A dog food of the present disclosure may additionally comprise other additives such as palatability enhancers and stabilizers in amounts and combinations familiar to one of skill in the art. Stabilizing substances include, for example, substances that tend to increase the shelf life of the composition. Other examples of other such additive potentially suitable for inclusion in the compositions of the invention include, for example, preservatives, colorants, antioxidants, flavorants, synergists and sequestrants, packaging gases, stabilizers, emulsifiers, thickeners, gelling agents, and humectants. Examples of emulsifiers and/or thickening agents include, for example, gelatin, cellulose ethers, starch, starch esters, starch ethers, and modified starches. The concentration of such additives in the composition typically may be up to about 5% by weight. In some embodiments, the concentration of such additives (particularly where such additives are primarily nutritional balancing agents, such as vitamins and minerals) is from about 0% to about 5% by weight. In some embodiments, the concentration of such additives (again, particularly where such additives are primarily nutritional balancing agents) is from about 0% to about 3% by weight.

A dog food of the present disclosure of any consistency or moisture content is contemplated, e.g., a dry, moist or semi-moist dog food. In some embodiments, the moisture content is from about 3% to about 90% of the total weight of the composition. "Semi-moist" refers to a dog food that has a moisture content from about 25 to about 35%. "Moist" food refers to a dog food that has a moisture content of from about 60 to about 90% or greater. "Dry" food refers to a dog food that has a moisture content of from about 3 to about 11% and may be manufactured in the form of small bits or kibbles.

As used herein, "kibble" includes a particulate pellet-like component dog food. Kibbles may range in texture from hard to soft and may have internal structures ranging from expanded structures to dense structures.

In preparing a dog food of the present disclosure in wet or canned form, any ingredient generally may, for example, be incorporated into the composition during the processing of the formulation, such as during and/or after mixing of other components of the composition. Distribution of these components into the composition may be accomplished by conventional means. In one embodiment, ground animal and poultry proteinaceous tissues are mixed with the other ingredients, including fish oils, cereal grains, other nutritionally balancing ingredients, special-purpose additives (e.g., vitamin and mineral mixtures, inorganic salts, cellulose and beet pulp, bulking agents, and the like) and water that is sufficient for processing is also added. These ingredients preferably are mixed in a vessel suitable for heating while blending the components. Heating of the mixture may be effected using any suitable manner, such as, for example, by direct steam injection or by using a vessel fitted with a heat exchanger. Following the addition of the last ingredient, the mixture is heated to a temperature range of from about 50° F. (10° C.) to about 212° F. (100° C.). In some embodiments, the mixture is heated to a temperature range of from about 70° F. (21° C.) to about 140° F. (60° C.). Temperatures outside these ranges are generally acceptable, but may be commercially impractical without use of other processing aids. When heated to the appropriate temperature, the material will typically be in the form of a thick liquid. The thick liquid is filled into cans. A lid is applied, and the container is hermetically sealed. The sealed can is then placed into conventional equipment designed to sterilize the contents. This is usually accomplished by heating to temperatures of greater than about 230° F. (110° C.) for an appropriate time, which is dependent on, for example, the temperature used and the composition.

A dog food of the present disclosure may alternatively be prepared in a dry form using conventional processes. Typically, dry ingredients, including, for example, animal protein, plant protein, grains, etc., are ground and mixed together. Moist or liquid ingredients, including fats, oils, animal protein, water, etc., are then added to and mixed with the dry mix. The mixture is then processed into kibbles or similar dry pieces. Kibble is often formed using an extrusion process in which the mixture of dry and wet ingredients is subjected to mechanical work at a high pressure and temperature, and forced through small openings and cut off into kibble by a rotating knife. The wet kibble is then dried and optionally coated with one or more topical coatings which may include, for example, flavors, fats, oils, powders, and the like. Kibble also can be made from the dough using a baking process, rather than extrusion, wherein the dough is placed into a mold before dry-heat processing.

A treat of the present disclosure may be prepared by, for example, an extrusion or baking process similar to those described above for dry food.

Treats include, for example, compositions that are given to an animal to entice the animal to eat during a non-meal time. Contemplated treats for dogs include, for example, dog bones. Treats may be nutritional, wherein the composition comprises one or more nutrients, and may, for example, have a composition as described above for food. Non-nutritional treats encompass any other treats that are non-toxic.

In one embodiment provided is a method for improving kidney function in a dog in need thereof comprising administering to the dog a composition comprising an effective amount of L-carnitine and one or both of eicosapentaenoic acid (EPA) and docosahexaenoic acid (DHA) (Method 1).

Further provided is Method 1 as follows:
1.1 Method 1 wherein the composition comprises at least 100 ppm L-carnitine.
1.2 Method 1 or 1.1 wherein the composition comprises at least 200 ppm L-carnitine.
1.3 Method 1, 1.1, or 1.2 wherein the composition comprises at least 300 ppm L-carnitine.
1.4 Method 1 or 1.1-1.3 wherein the composition comprises 100 ppm to 1500 ppm L-carnitine.
1.5 Method 1 or 1.1-1.4 wherein the composition comprises 200 ppm to 1500 ppm L-carnitine.
1.6 Method 1 or 1.1-1.5 wherein the composition comprises 200 ppm to 1200 ppm L-carnitine.
1.7 Method 1 or 1.1-1.6 wherein the composition comprises 200 ppm to 1000 ppm L-carnitine.
1.8 Method 1 or 1.1-1.7 wherein the composition comprises 200 ppm to 800 ppm L-carnitine.
1.9 Method 1 or 1.1-1.8 wherein the composition comprises 200 ppm to 700 ppm L-carnitine.
1.10 Method 1 or 1.1-1.9 wherein the composition comprises 300 ppm to 600 ppm L-carnitine.
1.11 Method 1 or 1.1-1.10 wherein the composition comprises 300 ppm L-carnitine.
1.12 Method 1 or 1.1-1.11 wherein the composition comprises at least 0.10 weight % of one or both of EPA and DHA.
1.13 Method 1 or 1.1-1.12 wherein the composition comprises at least 0.15 weight % of one or both of EPA and DHA.
1.14 Method 1 or 1.1-1.13 wherein the composition comprises at least 0.20 weight % of one or both of EPA and DHA.
1.15 Method 1 or 1.1-1.14 wherein the composition comprises at least 0.30 weight % of one or both of EPA and DHA.
1.16 Method 1 or 1.1-1.15 wherein the composition comprises at least 0.35 weight % of one or both of EPA and DHA.
1.17 Method 1 or 1.1-1.16 wherein the composition comprises at least 0.40 weight % of one or both of EPA and DHA.
1.18 Method 1 or 1.1-1.17 wherein the composition comprises at least 0.50 weight % of one or both of EPA and DHA.
1.19 Method 1 or 1.1-1.11 wherein the composition comprises at least 0.10 weight % of EPA.
1.20 Method 1.19 wherein the composition comprises at least 0.15 weight % of EPA.
1.21 Method 1.20 wherein the composition comprises at least 0.20 weight % of EPA.
1.22 Method 1.21 wherein the composition comprises at least 0.25 weight % of EPA.
1.23 Method 1.22 wherein the composition comprises at least 0.30 weight % of EPA.
1.24 Method 1, 1.1-1.11, or 1.19-1.23 wherein the composition comprises at least 0.05 weight % of DHA.

1.25 Method 1.24 wherein the composition comprises at least 0.10 weight % of DHA.
1.26 Method 1.25 wherein the composition comprises at least 0.15 weight % of DHA.
1.27 Method 1.26 wherein the composition comprises at least 0.20 weight % of DHA.
1.28 Method 1 or 1.1-1.27 wherein the composition comprises at least 0.10 weight % EPA and at least 0.05 weight % DHA.
1.29 Method 1.28 wherein the composition comprises at least 0.10 weight % EPA and at least 0.07 weight % DHA.
1.30 Method 1.29 wherein the composition comprises at least 0.20 weight % EPA and at least 0.15 weight % DHA.
1.31 Method 1.30 wherein the composition comprises at least 0.23 weight % EPA and at least 0.16 weight % DHA.
1.32 Method 1 or 1.1-1.31 wherein the composition comprises 0.10 weight % to 2.0 weight % of one or both of EPA and DHA.
1.33 Method 1.32 wherein the composition comprises 0.10 weight % to 1.5 weight % of one or both of EPA and DHA.
1.34 Method 1.33 wherein the composition comprises 0.15 weight % to 1.0 weight % of one or both of EPA and DHA.
1.35 Method 1.34 wherein the composition comprises 0.15 weight % to 0.50 weight % of one or both of EPA and DHA.
1.36 Method 1.35 wherein the composition comprises 0.15 weight % to 0.40 weight % of one or both of EPA and DHA.
1.37 Method 1 or 1.1-1.36 wherein the composition comprises 0.10 weight % to 2.0 weight % EPA.
1.38 Method 1.37 wherein the composition comprises 0.10 weight % to 1.5 weight % EPA.
1.39 Method 1.38 wherein the composition comprises 0.10 weight % to 1.0 weight % EPA.
1.40 Method 1.39 wherein the composition comprises 0.10 weight % to 0.80 weight % EPA.
1.41 Method 1.40 wherein the composition comprises 0.10 weight % to 0.60 weight % EPA.
1.42 Method 1.41 wherein the composition comprises 0.10 weight % to 0.40 weight % EPA.
1.43 Method 1.42 wherein the composition comprises 0.10 weight % to 0.30 weight % EPA.
1.44 Method 1 or 1.1-1.43 wherein the composition comprises 0.05 weight % to 2.0 weight % DHA.
1.45 Method 1.44 wherein the composition comprises 0.05 weight % to 1.5 weight % DHA.
1.46 Method 1.45 wherein the composition comprises 0.05 weight % to 1.0 weight % DHA.
1.47 Method 1.46 wherein the composition comprises 0.05 weight % to 0.80 weight % DHA.
1.48 Method 1.47 wherein the composition comprises 0.05 weight % to 0.60 weight % DHA.
1.49 Method 1.48 wherein the composition comprises 0.05 weight % to 0.40 weight % DHA.
1.50 Method 1.49 wherein the composition comprises 0.05 weight % to 0.20 weight % DHA.
1.51 Method 1.50 wherein the composition comprises 0.10 weight % to 0.20 weight % DHA.
1.52 Method 1 or 1.1-1.51 wherein the composition comprises at least 0.20 weight % fish oil.
1.53 Method 1 or 1.1-1.52 wherein the composition comprises at least 0.50 weight % fish oil.
1.54 Method 1 or 1.1-1.53 wherein the composition comprises at least 0.60 weight % fish oil.
1.55 Method 1 or 1.1-1.54 wherein the composition comprises at least 0.80 weight % fish oil.
1.56 Method 1 or 1.1-1.55 wherein the composition comprises at least 1.0 weight % fish oil.
1.57 Method 1 or 1.1-1.56 wherein the composition comprises at least 1.2 weight % fish oil.
1.58 Method 1 or 1.1-1.57 wherein the composition comprises at least 1.4 weight % fish oil.
1.59 Method 1 or 1.1-1.58 wherein the composition comprises at least 1.5 weight % fish oil.
1.60 Method 1 or 1.1-1.59 wherein the composition comprises at least 1.6 weight % fish oil.
1.61 Method 1 or 1.1-1.60 wherein the composition comprises at least 1.8 weight % fish oil.
1.62 Method 1 or 1.1-1.61 wherein the composition comprises at least 2.0 weight % fish oil.
1.63 Method 1 or 1.1-1.62 wherein the composition comprises at least 2.5 weight % fish oil.
1.64 Method 1 or 1.1-1.63 wherein the composition comprises at least 3.0 weight % fish oil.
1.65 Method 1 or 1.1-1.64 wherein the composition comprises 0.2 weight % to 3.0 weight % fish oil.
1.66 Method 1 or 1.1-1.65 wherein the composition comprises 0.2 weight % to 2.0 weight % fish oil.
1.67 Method 1 or 1.1-1.66 wherein the composition comprises 0.4 weight % to 2.0 weight % fish oil.
1.68 Method 1 or 1.1-1.67 wherein the composition comprises 0.6 weight % to 1.5 weight % fish oil.
1.69 Method 1 or 1.1-1.68 wherein the composition comprises at least 0.10 weight % of one or more medium chain fatty acids.
1.70 Method 1 or 1.1-1.69 wherein the composition comprises at least 0.15 weight % of one or more medium chain fatty acids.
1.71 Method 1 or 1.1-1.70 wherein the composition comprises at least 0.20 weight % of one or more medium chain fatty acids.
1.72 Method 1 or 1.1-1.71 wherein the composition comprises at least 0.70 weight % of one or more medium chain fatty acids.
1.73 Method 1 or 1.1-1.72 wherein the composition comprises at least 0.90 weight % of one or more medium chain fatty acids.
1.74 Method 1 or 1.1-1.73 wherein the composition comprises at least 1.0 weight % of one or more medium chain fatty acids.
1.75 Method 1 or 1.1-1.74 wherein the composition comprises at least 1.3 weight % of one or more medium chain fatty acids.
1.76 Method 1 or 1.1-1.75 wherein the composition comprises at least 1.4 weight % of on or more medium chain fatty acids.
1.77 Method 1 or 1.1-1.76 wherein the composition comprises at least 1.7 weight % of one or more medium chain fatty acids.
1.78 Method 1 or 1.1-1.77 wherein the composition comprises at least 1.9 weight % of one or more medium chain fatty acids.
1.79 Method 1 or 1.1-1.78 wherein the composition comprises at least 2.0 weight % of one or more medium chain fatty acids.
1.80 Method 1 or 1.1-1.79 wherein the composition comprises at least 3.0 weight % of one or more medium chain fatty acids.

1.81 Method 1 or 1.1-1.80 wherein the composition comprises 0.10 weight % to 3.0 weight % of one or more medium chain fatty acids.
1.82 Method 1 or 1.1-1.81 wherein the composition comprises 0.10 weight % to 2.5 weight % of one or more medium chain fatty acids.
1.83 Method 1 or 1.1-1.82 wherein the composition comprises 0.10 weight % to 2.0 weight % of one or more medium chain fatty acids.
1.84 Method 1 or 1.1-1.83 wherein the composition comprises 0.30 weight % to 2.0 weight % of one or more medium chain fatty acids.
1.85 Method 1 or 1.1-1.84 wherein the composition comprises 0.50 weight % to 2.0 weight % of one or more medium chain fatty acids.
1.86 Method 1.69-1.85 wherein the one or more medium chain fatty acids are selected from capric acid, lauric acid, and myristic acid.
1.87 Method 1 or 1.1-1.86 wherein the composition comprises at least 0.10 weight % capric acid.
1.88 Method 1 or 1.1-1.87 wherein the composition comprises at least 0.20 weight % capric acid.
1.89 Method 1 or 1.1-1.88 wherein the composition comprises at least 0.40 weight % capric acid.
1.90 Method 1 or 1.1-1.89 wherein the composition comprises at least 0.60 weight % capric acid.
1.91 Method 1 or 1.1-1.90 wherein the composition comprises at least 0.80 weight % capric acid.
1.92 Method 1 or 1.1-1.91 wherein the composition comprises at least 1.0 weight % capric acid.
1.93 Method 1 or 1.1-1.92 wherein the composition comprises at least 2.0 weight % capric acid.
1.94 Method 1 or 1.1-1.93 wherein the composition comprises 0.10 weight % to 2.0 weight % capric acid.
1.95 Method 1.94 wherein the composition comprises 0.10 weight % to 1.0 weight % capric acid.
1.96 Method 1.95 wherein the composition comprises 0.10 weight % to 0.80 weight % capric acid.
1.97 Method 1.96 wherein the composition comprises 0.10 weight % to 0.60 weight % capric acid.
1.98 Method 1.97 wherein the composition comprises 0.10 weight % to 0.40 weight % capric acid.
1.99 Method 1.98 wherein the composition comprises 0.10 weight % to 0.20 weight % capric acid.
1.100 Method 1 or 1.1-1.99 wherein the composition comprises at least 0.10 weight % lauric acid.
1.101 Method 1 or 1.1-1.100 wherein the composition comprises at least 0.20 weight % lauric acid.
1.102 Method 1 or 1.1-1.101 wherein the composition comprises at least 0.40 weight % lauric acid.
1.103 Method 1 or 1.1-1.102 wherein the composition comprises at least 0.60 weight % lauric acid.
1.104 Method 1 or 1.1-1.103 wherein the composition comprises at least 0.80 weight % lauric acid.
1.105 Method 1 or 1.1-1.104 wherein the composition comprises at least 1.0 weight % lauric acid.
1.106 Method 1 or 1.1-1.105 wherein the composition comprises at least 2.0 weight % lauric acid.
1.107 Method 1 or 1.1-1.106 wherein the composition comprises at least 3.0 weight % lauric acid.
1.108 Method 1 or 1.1-1.107 wherein the composition comprises 0.10 weight % to 3.0 weight % lauric acid.
1.109 Method 1.108 wherein the composition comprises 0.10 weight % to 2.0 weight % lauric acid.
1.110 Method 1.109 wherein the composition comprises 0.10 weight % to 1.5 weight % lauric acid.
1.111 Method 1.110 wherein the composition comprises 0.10 weight % to 1.0 weight % lauric acid.
1.112 Method 1.111 wherein the composition comprises 0.10 weight % to 3.0 weight % lauric acid.
1.113 Method 1 or 1.1-1.68 wherein the composition comprises one or more medium chain triglyceride oils.
1.114 Method 1.113 wherein the composition comprises at least 1 weight % of one or more medium chain triglyceride oils.
1.115 Method 1.114 wherein the composition comprises at least 2 weight % of one or more medium chain triglyceride oils.
1.116 Method 1.115 wherein the composition comprises at least 4 weight % of one or more medium chain triglyceride oils.
1.117 Method 1.116 wherein the composition comprises at least 6 weight % of one or more medium chain triglyceride oils.
1.118 Method 1.117 wherein the composition comprises at least 8 weight % of one or more medium chain triglyceride oils.
1.119 Method 1.118 wherein the composition comprises at least 10 weight % of one or more medium chain triglyceride oils.
1.120 Method 1.119 wherein the composition comprises at least 12 weight % of one or more medium chain triglyceride oils.
1.121 Method 1.120 wherein the composition comprises at least 15 weight % of one or more medium chain triglyceride oils.
1.122 Method 1.121 wherein the composition comprises at least 20 weight % of one or more medium chain triglyceride oils.
1.123 Method 1.113 wherein the composition comprises 1 weight % to 10 weight % of one or more medium chain triglyceride oils.
1.124 Method 1.123 wherein the composition comprises 1 weight % to 15 weight % of one or more medium chain triglyceride oils.
1.125 Method 1.124 wherein the composition comprises 1 weight % to 10 weight % of one or more medium chain triglyceride oils.
1.126 Method 1.113-1.125 wherein the one or more medium chain triglyceride oil is coconut oil.
1.127 Method 1 or 1.1-1.126 wherein the composition comprises 1 weight % to 10 weight % coconut oil.
1.128 Method 1.127 wherein the composition comprises 2 weight % to 8 weight % coconut oil.
1.129 Method 1.128 wherein the composition comprises 2 weight % to 5 weight % coconut oil.
1.130 Method 1 or 1.1-1.129 wherein the composition comprises 1 weight % to 15 weight % corn oil.
1.131 Method 1.130 wherein the composition comprises 2 weight % to 10 weight % corn oil.
1.132 Method 1.131 wherein the composition comprises 5 weight % to 10 weight % corn oil.
1.133 Method 1 or 1.1-1.132 wherein the composition comprises at least 2 weight % linoleic acid (LA).
1.134 Method 1.133 wherein the composition comprises at least 3 weight % linoleic acid (LA).
1.135 Method 1.134 wherein the composition comprises at least 4 weight % linoleic acid (LA).
1.136 Method 1.135 wherein the composition comprises at least 5 weight % linoleic acid (LA).
1.137 Method 1.136 wherein the composition comprises at least 8 weight % linoleic acid (LA).

1.138 Method 1.137 wherein the composition comprises at least 10 weight % linoleic acid (LA).
1.139 Method 1 or 1.1-1.138 wherein the composition comprises 2 weight % to 10 weight % linoleic acid.
1.140 Method 1.139 wherein the composition comprises 3 weight % to 8 weight % linoleic acid.
1.141 Method 1.140 wherein the composition comprises 4 weight % to 6 weight % linoleic acid.
1.142 Method 1.141 wherein the composition comprises weight 4% to 5 weight % linoleic acid.
1.143 Method 1 or 1.1-1.142 wherein the composition comprises at least 1.5 weight % α-linolenic acid, e.g., from 1.5 weight % to 10 weight %, e.g, from 1.5 weight % to 8 weight %, e.g., from 1.5 weight % to 5 weight %, e.g., from 1.5 to 3 weight %.
1.144 Method 1 or 1.1-1.143 wherein the composition comprises arachidonic acid.
1.145 Method 1 or 1.1-1.144 wherein the composition comprises a ratio of eicosapentaenoic acid to arachidonic acid of 1.2:1 or greater.
1.146 Method 1.145 wherein the composition comprises a ratio of eicosapentaenoic acid to arachidonic acid of 1.3:1 or greater.
1.147 Method 1.146 wherein the composition comprises a ratio of eicosapentaenoic acid to arachidonic acid of 1.5:1 or greater.
1.148 Method 1.147 wherein the composition comprises a ratio of eicosapentaenoic acid to arachidonic acid of 2:1 or greater.
1.149 Method 1.148 wherein the composition comprises a ratio of eicosapentaenoic acid to arachidonic acid of 3:1 or greater.
1.150 Method 1.149 wherein the composition comprises a ratio of eicosapentaenoic acid to arachidonic acid of 3.5:1 or greater.
1.151 Method 1.150 wherein the composition comprises a ratio of eicosapentaenoic acid to arachidonic acid of 3.8:1 or greater.
1.152 Method 1.151 wherein the composition comprises a ratio of eicosapentaenoic acid to arachidonic acid of 4:1 or greater.
1.153 Method 1 or 1.1-1.152 wherein the composition comprises 0.01 weight % to 0.5 weight % arachidonic acid.
1.154 Method 1.153 wherein the composition comprises 0.01 weight % to 0.1 weight % arachidonic acid.
1.155 Method 1.154 wherein the composition comprises 0.01 weight % to 0.08 weight % arachidonic acid.
1.156 Method 1.155 wherein the composition comprises 0.02 weight % to 0.07 weight % arachidonic acid.
1.157 Method 1.156 wherein the composition comprises 0.03 weight % to 0.07 weight % arachidonic acid.
1.158 Method 1.157 wherein the composition comprises 0.04 weight % to 0.06 weight % arachidonic acid.
1.159 Method 1.158 wherein the composition comprises 0.06 weight % arachidonic acid.
1.160 Method 1 or 1.1-1.159 wherein the composition is a dog food.
1.161 Method 1.160 wherein the composition comprises one or more of protein, fiber, and nutritional balancing agents.
1.162 Method 1.161 wherein the composition comprises at least 10% protein, at least 10% fat, and at least 0.5% crude fiber.
1.163 Method 1.162 wherein the composition comprises at least 15% fat and at least 1.0% crude fiber.
1.164 Method 1.158-1.163 wherein the composition comprises at least 0.50% calcium, 0.10% phosphorus, and 0.1% sodium.
1.165 Method 1.164 wherein the composition comprises at least 0.70% calcium, 0.20% phosphorus, and 0.2% sodium.
1.166 Method 1.158-1.165 wherein the composition comprises at least 1.0% alpha-linoleic acid (α-LA).
1.167 Method 1.166 wherein the composition comprises at least 1.0% alpha-linoleic acid (α-LA).
1.168 Method 1.167 wherein the composition comprises at least 1.5% alpha-linoleic acid (α-LA).
1.169 Method 1 or 1.1-1.168 wherein the composition comprises at least 4.0% of one or more saturated fatty acids.
1.170 Method 1.169 wherein the composition comprises at least 4.5% of one or more saturated fatty acids.
1.171 Method 1 or 1.1-1.170 wherein the composition comprises at least 5.0% or one or more monounsaturated fatty acids.
1.172 Method 1 or 1.1-1.171 wherein the composition comprises at least 4.0% of one or more polyunsaturated fatty acids.
1.173 Method 1 or 1.1-1.172 wherein the composition comprises at least 3.0% of omega-6 fatty acids (n-6 fatty acids) and at least 1.0% of omega-3 fatty acids (n-3 fatty acids).
1.174 Method 1 or 1.1-1.159 wherein the composition is a dog treat.
1.175 Method 1 or 1.1-1.174 wherein the composition comprises one or more renal drugs.
1.176 Method 1 or 1.1-1.175 wherein the composition is administered in conjunction with one or more renal drugs.

In another embodiment provided is a method for the treatment or prophylaxis of kidney disease in a dog in need thereof comprising administering to the dog a composition comprising an effective amount of L-carnitine and one or both of eicosapentaenoic acid (EPA) and docosahexaenoic acid (DHA) (Method 2).

Further provided is Method 2 as follows:
2.1 Method 2 wherein the composition comprises at least 100 ppm L-carnitine.
2.2 Method 2 or 2.1 wherein the composition comprises at least 200 ppm L-carnitine.
2.3 Method 2, 2.1, or 2.2 wherein the composition comprises at least 300 ppm L-carnitine.
2.4 Method 2 or 2.1-2.3 wherein the composition comprises 100 ppm to 1500 ppm L-carnitine.
2.5 Method 2 or 2.1-2.4 wherein the composition comprises 200 ppm to 1500 ppm L-carnitine.
2.6 Method 2 or 2.1-2.5 wherein the composition comprises 200 ppm to 1200 ppm L-carnitine.
2.7 Method 2 or 2.1-2.6 wherein the composition comprises 200 ppm to 1000 ppm L-carnitine.
2.8 Method 2 or 2.1-2.7 wherein the composition comprises 200 ppm to 800 ppm L-carnitine.
2.9 Method 2 or 2.1-2.8 wherein the composition comprises 200 ppm to 700 ppm L-carnitine.
2.10 Method 2 or 2.1-2.9 wherein the composition comprises 300 ppm to 600 ppm L-carnitine.
2.11 Method 2 or 2.1-2.10 wherein the composition comprises 300 ppm L-carnitine.
2.12 Method 2 or 2.1-2.11 wherein the composition comprises at least 0.10 weight % of one or both of EPA and DHA.

2.13 Method 2 or 2.1-2.12 wherein the composition comprises at least 0.15 weight % of one or both of EPA and DHA.
2.14 Method 2 or 2.1-2.13 wherein the composition comprises at least 0.20 weight % of one or both of EPA and DHA.
2.15 Method 2 or 2.1-2.14 wherein the composition comprises at least 0.30 weight % of one or both of EPA and DHA.
2.16 Method 2 or 2.1-2.15 wherein the composition comprises at least 0.35 weight % of one or both of EPA and DHA.
2.17 Method 2 or 2.1-2.16 wherein the composition comprises at least 0.40 weight % of one or both of EPA and DHA.
2.18 Method 2 or 2.1-2.17 wherein the composition comprises at least 0.50 weight % of one or both of EPA and DHA.
2.19 Method 2 or 2.1-2.11 wherein the composition comprises at least 0.10 weight % of EPA.
2.20 Method 2.19 wherein the composition comprises at least 0.15 weight % of EPA.
2.21 Method 2.20 wherein the composition comprises at least 0.20 weight % of EPA.
2.22 Method 2.21 wherein the composition comprises at least 0.25 weight % of EPA.
2.23 Method 2.22 wherein the composition comprises at least 0.30 weight % of EPA.
2.24 Method 2, 2.1-2.11, or 2.19-2.23 wherein the composition comprises at least 0.05 weight % of DHA.
2.25 Method 2.24 wherein the composition comprises at least 0.10 weight % of DHA.
2.26 Method 2.25 wherein the composition comprises at least 0.15 weight % of DHA.
2.27 Method 2.26 wherein the composition comprises at least 0.20 weight % of DHA.
2.28 Method 2 or 2.1-2.27 wherein the composition comprises at least 0.10 weight % EPA and at least 0.05 weight % DHA.
2.29 Method 2.28 wherein the composition comprises at least 0.10 weight % EPA and at least 0.07 weight % DHA.
2.30 Method 2.29 wherein the composition comprises at least 0.20 weight % EPA and at least 0.15 weight % DHA.
2.31 Method 2.30 wherein the composition comprises at least 0.23 weight % EPA and at least 0.16 weight % DHA.
2.32 Method 2 or 2.1-2.31 wherein the composition comprises 0.10 weight % to 2.0 weight % of one or both of EPA and DHA.
2.33 Method 2.32 wherein the composition comprises 0.10 weight % to 1.5 weight % of one or both of EPA and DHA.
2.34 Method 2.33 wherein the composition comprises 0.15 weight % to 1.0 weight % of one or both of EPA and DHA.
2.35 Method 2.34 wherein the composition comprises 0.15 weight % to 0.50 weight % of one or both of EPA and DHA.
2.36 Method 2.35 wherein the composition comprises 0.15 weight % to 0.40 weight % of one or both of EPA and DHA.
2.37 Method 2 or 2.1-2.36 wherein the composition comprises 0.10 weight % to 2.0 weight % EPA.
2.38 Method 2.37 wherein the composition comprises 0.10 weight % to 1.5 weight % EPA.
2.39 Method 2.38 wherein the composition comprises 0.10 weight % to 1.0 weight % EPA.
2.40 Method 2.39 wherein the composition comprises 0.10 weight % to 0.80 weight % EPA.
2.41 Method 2.40 wherein the composition comprises 0.10 weight % to 0.60 weight % EPA.
2.42 Method 2.41 wherein the composition comprises 0.10 weight % to 0.40 weight % EPA.
2.43 Method 2.42 wherein the composition comprises 0.10 weight % to 0.30 weight % EPA.
2.44 Method 2 or 2.1-2.43 wherein the composition comprises 0.05 weight % to 2.0 weight % DHA.
2.45 Method 2.44 wherein the composition comprises 0.05 weight % to 1.5 weight % DHA.
2.46 Method 2.45 wherein the composition comprises 0.05 weight % to 1.0 weight % DHA.
2.47 Method 2.46 wherein the composition comprises 0.05 weight % to 0.80 weight % DHA.
2.48 Method 2.47 wherein the composition comprises 0.05 weight % to 0.60 weight % DHA.
2.49 Method 2.48 wherein the composition comprises 0.05 weight % to 0.40 weight % DHA.
2.50 Method 2.49 wherein the composition comprises 0.05 weight % to 0.20 weight % DHA.
2.51 Method 2.50 wherein the composition comprises 0.10 weight % to 0.20 weight % DHA.
2.52 Method 2 or 2.1-2.51 wherein the composition comprises at least 0.20 weight % fish oil.
2.53 Method 2 or 2.1-2.52 wherein the composition comprises at least 0.50 weight % fish oil.
2.54 Method 2 or 2.1-2.53 wherein the composition comprises at least 0.60 weight % fish oil.
2.55 Method 2 or 2.1-2.54 wherein the composition comprises at least 0.80 weight % fish oil.
2.56 Method 2 or 2.1-2.55 wherein the composition comprises at least 1.0 weight % fish oil.
2.57 Method 2 or 2.1-2.56 wherein the composition comprises at least 1.2 weight % fish oil.
2.58 Method 2 or 2.1-2.57 wherein the composition comprises at least 1.4 weight % fish oil.
2.59 Method 2 or 2.1-2.58 wherein the composition comprises at least 1.5 weight % fish oil.
2.60 Method 2 or 2.1-2.59 wherein the composition comprises at least 1.6 weight % fish oil.
2.61 Method 2 or 2.1-2.60 wherein the composition comprises at least 1.8 weight % fish oil.
2.62 Method 2 or 2.1-2.61 wherein the composition comprises at least 2.0 weight % fish oil.
2.63 Method 2 or 2.1-2.62 wherein the composition comprises at least 2.5 weight % fish oil.
2.64 Method 2 or 2.1-2.63 wherein the composition comprises at least 3.0 weight % fish oil.
2.65 Method 2 or 2.1-2.64 wherein the composition comprises 0.2 weight % to 3.0 weight % fish oil.
2.66 Method 2 or 2.1-2.65 wherein the composition comprises 0.2 weight % to 2.0 weight % fish oil.
2.67 Method 2 or 2.1-2.66 wherein the composition comprises 0.4 weight % to 2.0 weight % fish oil.
2.68 Method 2 or 2.1-2.67 wherein the composition comprises 0.6 weight % to 1.5 weight % fish oil.
2.69 Method 2 or 2.1-1.68 wherein the composition comprises at least 0.10 weight % of one or more medium chain fatty acids.
2.70 Method 2 or 2.1-2.69 wherein the composition comprises at least 0.15 weight % of one or more medium chain fatty acids.

2.71 Method 2 or 2.1-2.70 wherein the composition comprises at least 0.20 weight % of one or more medium chain fatty acids.
2.72 Method 2 or 2.1-2.71 wherein the composition comprises at least 0.70 weight % of one or more medium chain fatty acids.
2.73 Method 2 or 2.1-2.72 wherein the composition comprises at least 0.90 weight % of one or more medium chain fatty acids.
2.74 Method 2 or 2.1-2.73 wherein the composition comprises at least 1.0 weight % of one or more medium chain fatty acids.
2.75 Method 2 or 2.1-2.74 wherein the composition comprises at least 1.3 weight % of one or more medium chain fatty acids.
2.76 Method 2 or 2.1-2.75 wherein the composition comprises at least 1.4 weight % of on or more medium chain fatty acids.
2.77 Method 2 or 2.1-2.76 wherein the composition comprises at least 1.7 weight % of one or more medium chain fatty acids.
2.78 Method 2 or 2.1-2.77 wherein the composition comprises at least 1.9 weight % of one or more medium chain fatty acids.
2.79 Method 2 or 2.1-2.78 wherein the composition comprises at least 2.0 weight % of one or more medium chain fatty acids.
2.80 Method 2 or 2.1-2.79 wherein the composition comprises at least 3.0 weight % of one or more medium chain fatty acids.
2.81 Method 2 or 2.1-2.80 wherein the composition comprises 0.10 weight % to 3.0 weight % of one or more medium chain fatty acids.
2.82 Method 2 or 2.1-2.81 wherein the composition comprises 0.10 weight % to 2.5 weight % of one or more medium chain fatty acids.
2.83 Method 2 or 2.1-2.82 wherein the composition comprises 0.10 weight % to 2.0 weight % of one or more medium chain fatty acids.
2.84 Method 2 or 2.1-2.83 wherein the composition comprises 0.30 weight % to 2.0 weight % of one or more medium chain fatty acids.
2.85 Method 2 or 2.1-2.84 wherein the composition comprises 0.50 weight % to 2.0 weight % of one or more medium chain fatty acids.
2.86 Method 2.69-2.85 wherein the one or more medium chain fatty acids are selected from capric acid, lauric acid, and myristic acid.
2.87 Method 2 or 2.1-2.86 wherein the composition comprises at least 0.10 weight % capric acid.
2.88 Method 2 or 2.1-2.87 wherein the composition comprises at least 0.20 weight % capric acid.
2.89 Method 2 or 2.1-2.88 wherein the composition comprises at least 0.40 weight % capric acid.
2.90 Method 2 or 2.1-2.89 wherein the composition comprises at least 0.60 weight % capric acid.
2.91 Method 2 or 2.1-2.90 wherein the composition comprises at least 0.80 weight % capric acid.
2.92 Method 2 or 2.1-2.91 wherein the composition comprises at least 1.0 weight % capric acid.
2.93 Method 2 or 2.1-2.92 wherein the composition comprises at least 2.0 weight % capric acid.
2.94 Method 2 or 2.1-2.93 wherein the composition comprises 0.10 weight % to 2.0 weight % capric acid.
2.95 Method 2.94 wherein the composition comprises 0.10 weight % to 1.0 weight % capric acid.
2.96 Method 2.95 wherein the composition comprises 0.10 weight % to 0.80 weight % capric acid.
2.97 Method 2.96 wherein the composition comprises 0.10 weight % to 0.60 weight % capric acid.
2.98 Method 2.97 wherein the composition comprises 0.10 weight % to 0.40 weight % capric acid.
2.99 Method 2.98 wherein the composition comprises 0.10 weight % to 0.20 weight % capric acid.
2.100 Method 2 or 2.1-2.99 wherein the composition comprises at least 0.10 weight % lauric acid.
2.101 Method 2 or 2.1-2.100 wherein the composition comprises at least 0.20 weight % lauric acid.
2.102 Method 2 or 2.1-2.101 wherein the composition comprises at least 0.40 weight % lauric acid.
2.103 Method 2 or 2.1-2.102 wherein the composition comprises at least 0.60 weight % lauric acid.
2.104 Method 2 or 2.1-2.103 wherein the composition comprises at least 0.80 weight % lauric acid.
2.105 Method 2 or 2.1-2.104 wherein the composition comprises at least 1.0 weight % lauric acid.
2.106 Method 2 or 2.1-2.105 wherein the composition comprises at least 2.0 weight % lauric acid.
2.107 Method 2 or 2.1-2.106 wherein the composition comprises at least 3.0 weight % lauric acid.
2.108 Method 2 or 2.1-2.107 wherein the composition comprises 0.10 weight % to 3.0 weight % lauric acid.
2.109 Method 2.108 wherein the composition comprises 0.10 weight % to 2.0 weight % lauric acid.
2.110 Method 2.109 wherein the composition comprises 0.10 weight % to 1.5 weight % lauric acid.
2.111 Method 2.110 wherein the composition comprises 0.10 weight % to 1.0 weight % lauric acid.
2.112 Method 2.111 wherein the composition comprises 0.10 weight % to 3.0 weight % lauric acid.
2.113 Method 2 or 2.1-2.68 wherein the composition comprises one or more medium chain triglyceride oils.
2.114 Method 2.113 wherein the composition comprises at least 1 weight % of one or more medium chain triglyceride oils.
2.115 Method 2.114 wherein the composition comprises at least 2 weight % of one or more medium chain triglyceride oils.
2.116 Method 2.115 wherein the composition comprises at least 4 weight % of one or more medium chain triglyceride oils.
2.117 Method 2.116 wherein the composition comprises at least 6 weight % of one or more medium chain triglyceride oils.
2.118 Method 2.117 wherein the composition comprises at least 8 weight % of one or more medium chain triglyceride oils.
2.119 Method 2.118 wherein the composition comprises at least 10 weight % of one or more medium chain triglyceride oils.
2.120 Method 2.119 wherein the composition comprises at least 12 weight % of one or more medium chain triglyceride oils.
2.121 Method 2.120 wherein the composition comprises at least 15 weight % of one or more medium chain triglyceride oils.
2.122 Method 2.121 wherein the composition comprises at least 20 weight % of one or more medium chain triglyceride oils.
2.123 Method 2.113 wherein the composition comprises 1 weight % to 20 weight % of one or more medium chain triglyceride oils.

2.124 Method 2.123 wherein the composition comprises 1 weight % to 15 weight % of one or more medium chain triglyceride oils.
2.125 Method 2.124 wherein the composition comprises 1 weight % to 10 weight % of one or more medium chain triglyceride oils.
2.126 Method 2.113-2.125 wherein the one or more medium chain triglyceride oils is coconut oil.
2.127 Method 2 or 2.1-2.126 wherein the composition comprises 1 weight % to 10 weight % coconut oil.
2.128 Method 2.127 wherein the composition comprises 2 weight % to 8 weight % coconut oil.
2.129 Method 2.128 wherein the composition comprises 2 weight % to 5 weight % coconut oil.
2.130 Method 2 or 2.1-2.129 wherein the composition comprises 1 weight % to 15 weight % corn oil.
2.131 Method 2.130 wherein the composition comprises 2 weight % to 10 weight % corn oil.
2.132 Method 2.131 wherein the composition comprises 5 weight % to 10 weight % corn oil.
2.133 Method 2 or 2.1-2.132 wherein the composition comprises at least 2 weight % linoleic acid (LA).
2.134 Method 2.133 wherein the composition comprises at least 3 weight % linoleic acid (LA).
2.135 Method 2.134 wherein the composition comprises at least 4 weight % linoleic acid (LA).
2.136 Method 2.135 wherein the composition comprises at least 5 weight % linoleic acid (LA).
2.137 Method 2.136 wherein the composition comprises at least 8 weight % linoleic acid (LA).
2.138 Method 2.137 wherein the composition comprises at least 10 weight % linoleic acid (LA).
2.139 Method 2 or 2.1-2.138 wherein the composition comprises 2 weight % to 10 weight % linoleic acid.
2.140 Method 2.139 wherein the composition comprises 3 weight % to 8 weight % linoleic acid.
2.141 Method 2.140 wherein the composition comprises 4 weight % to 6 weight % linoleic acid.
2.142 Method 2.141 wherein the composition comprises 4 weight % to 5 weight % linoleic acid.
2.143 Method 2 or 2.1-2.142 wherein the composition comprises at least 1.5 weight % α-linolenic acid, e.g., from 1.5 weight % to 10 weight %, e.g, from 1.5 weight % to 8 weight %, e.g., from 1.5 weight % to 5 weight %, e.g., from 1.5 to 3 weight %.
2.144 Method 2 or 2.1-2.143 wherein the composition comprises arachidonic acid.
2.145 Method 2 or 2.1-2.144 wherein the composition comprises a ratio of eicosapentaenoic acid to arachidonic acid of 1.2:1 or greater.
2.146 Method 2.145 wherein the composition comprises a ratio of eicosapentaenoic acid to arachidonic acid of 1.3:1 or greater.
2.147 Method 2.146 wherein the composition comprises a ratio of eicosapentaenoic acid to arachidonic acid of 1.5:1 or greater.
2.148 Method 2.147 wherein the composition comprises a ratio of eicosapentaenoic acid to arachidonic acid of 2:1 or greater.
2.149 Method 2.148 wherein the composition comprises a ratio of eicosapentaenoic acid to arachidonic acid of 3:1 or greater.
2.150 Method 2.149 wherein the composition comprises a ratio of eicosapentaenoic acid to arachidonic acid of 3.5:1 or greater.
2.151 Method 2.150 wherein the composition comprises a ratio of eicosapentaenoic acid to arachidonic acid of 3.8:1 or greater.
2.152 Method 2.151 wherein the composition comprises a ratio of eicosapentaenoic acid to arachidonic acid of 4:1 or greater.
2.153 Method 2 or 2.1-2.152 wherein the composition comprises 0.01 weight % to 0.5 weight % arachidonic acid.
2.154 Method 2.153 wherein the composition comprises 0.01 weight % to 0.1 weight % arachidonic acid.
2.155 Method 2.154 wherein the composition comprises 0.01 weight % to 0.08 weight % arachidonic acid.
2.156 Method 2.155 wherein the composition comprises 0.02 weight % to 0.07 weight % arachidonic acid.
2.157 Method 2.156 wherein the composition comprises 0.03 weight % to 0.07 weight % arachidonic acid.
2.158 Method 2.157 wherein the composition comprises 0.04 weight % to 0.06 weight % arachidonic acid.
2.159 Method 2.158 wherein the composition comprises 0.06 weight % arachidonic acid.
2.160 Method 2 or 2.1-2.159 wherein the composition is a dog food.
2.161 Method 2.160 wherein the composition comprises one or more of protein, fiber, and nutritional balancing agents.
2.162 Method 2.161 wherein the composition comprises at least 10 weight % protein, at least 10 weight % fat, and at least 0.5 weight % crude fiber.
2.163 Method 2.162 wherein the composition comprises at least 15 weight % fat and at least 1.0 weight % crude fiber.
2.164 Method 2.158-2.163 wherein the composition comprises at least 0.50 weight % calcium, 0.10 weight % phosphorus, and 0.1 weight % sodium.
2.165 Method 2.164 wherein the composition comprises at least 0.70 weight % calcium, 0.20 weight % phosphorus, and 0.2 weight % sodium.
2.166 Method 2.158-2.165 wherein the composition comprises at least 1.0 weight % alpha-linoleic acid (α-LA).
2.167 Method 2.166 wherein the composition comprises at least 1.0 weight % alpha-linoleic acid (α-LA).
2.168 Method 2.167 wherein the composition comprises at least 1.5 weight % alpha-linoleic acid (α-LA).
2.169 Method 2 or 2.1-2.168 wherein the composition comprises at least 4.0 weight % of one or more saturated fatty acids.
2.170 Method 2.169 wherein the composition comprises at least 4.5 weight % of one or more saturated fatty acids.
2.171 Method 2 or 2.1-2.170 wherein the composition comprises at least 5.0 weight % or one or more monounsaturated fatty acids.
2.172 Method 2 or 2.1-2.171 wherein the composition comprises at least 4.0 weight % of one or more polyunsaturated fatty acids.
2.173 Method 2 or 2.1-2.172 wherein the composition comprises at least 3.0 weight % of omega-6 fatty acids (n-6 fatty acids) and at least 1.0 weight % of omega-3 fatty acids (n-3 fatty acids).
2.174 Method 2 or 2.1-2.159 wherein the composition is a dog treat.
2.175 Method 2 or 2.1-2.174 wherein the composition comprises one or more renal drugs.
2.176 Method 2 or 2.1-2.175 wherein the composition is administered in conjunction with one or more renal drugs.

In yet another embodiment provided is a composition comprising L-carnitine and one or both of eicosapentaenoic acid (EPA) and docosahexaenoic acid (DHA) in an amount effective to improve kidney function in a dog in need thereof (Composition 1).

Further provided is Composition 1 as follows:

1.1 Composition 1 wherein the composition comprises at least 100 ppm L-carnitine.
1.2 Composition 1 or 1.1 wherein the composition comprises at least 200 ppm L-carnitine.
1.3 Composition 1, 1.1, or 1.2 wherein the composition comprises at least 300 ppm L-carnitine.
1.4 Composition 1 or 1.1-1.3 wherein the composition comprises 100 ppm to 1500 ppm L-carnitine.
1.5 Composition 1 or 1.1-1.4 wherein the composition comprises 200 ppm to 1500 ppm L-carnitine.
1.6 Composition 1 or 1.1-1.5 wherein the composition comprises 200 ppm to 1200 ppm L-carnitine.
1.7 Composition 1 or 1.1-1.6 wherein the composition comprises 200 ppm to 1000 ppm L-carnitine.
1.8 Composition 1 or 1.1-1.7 wherein the composition comprises 200 ppm to 800 ppm L-carnitine.
1.9 Composition 1 or 1.1-1.8 wherein the composition comprises 200 ppm to 700 ppm L-carnitine.
1.10 Composition 1 or 1.1-1.9 wherein the composition comprises 300 ppm to 600 ppm L-carnitine.
1.11 Composition 1 or 1.1-1.10 wherein the composition comprises 300 ppm L-carnitine.
1.12 Composition 1 or 1.1-1.11 wherein the composition comprises at least 0.10 weight % of one or both of EPA and DHA.
1.13 Composition 1 or 1.1-1.12 wherein the composition comprises at least 0.15 weight % of one or both of EPA and DHA.
1.14 Composition 1 or 1.1-1.13 wherein the composition comprises at least 0.20 weight % of one or both of EPA and DHA.
1.15 Composition 1 or 1.1-1.14 wherein the composition comprises at least 0.30 weight % of one or both of EPA and DHA.
1.16 Composition 1 or 1.1-1.15 wherein the composition comprises at least 0.35 weight % of one or both of EPA and DHA.
1.17 Composition 1 or 1.1-1.16 wherein the composition comprises at least 0.40 weight % of one or both of EPA and DHA.
1.18 Composition 1 or 1.1-1.17 wherein the composition comprises at least 0.50 weight % of one or both of EPA and DHA.
1.19 Composition 1 or 1.1-1.11 wherein the composition comprises at least 0.10 weight % of EPA.
1.20 Composition 1.19 wherein the composition comprises at least 0.15 weight % of EPA.
1.21 Composition 1.20 wherein the composition comprises at least 0.20 weight % of EPA.
1.22 Composition 1.21 wherein the composition comprises at least 0.25 weight % of EPA.
1.23 Composition 1.22 wherein the composition comprises at least 0.30 weight % of EPA.
1.24 Composition 1, 1.1-1.11, or 1.19-1.23 wherein the composition comprises at least 0.05 weight % of DHA.
1.25 Composition 1.24 wherein the composition comprises at least 0.10 weight % of DHA.
1.26 Composition 1.25 wherein the composition comprises at least 0.15 weight % of DHA.
1.27 Composition 1.26 wherein the composition comprises at least 0.20 weight % of DHA.
1.28 Composition 1 or 1.1-1.27 wherein the composition comprises at least 0.10 weight % EPA and at least 0.05 weight % DHA.
1.29 Composition 1.28 wherein the composition comprises at least 0.10 weight % EPA and at least 0.07 weight % DHA.
1.30 Composition 1.29 wherein the composition comprises at least 0.20 weight % EPA and at least 0.15 weight % DHA.
1.31 Composition 1.30 wherein the composition comprises at least 0.23 weight % EPA and at least 0.16 weight % DHA.
1.32 Composition 1 or 1.1-1.31 wherein the composition comprises 0.10 weight % to 2.0 weight % of one or both of EPA and DHA.
1.33 Composition 1.32 wherein the composition comprises 0.10 weight % to 1.5 weight % of one or both of EPA and DHA.
1.34 Composition 1.33 wherein the composition comprises 0.15 weight % to 1.0 weight % of one or both of EPA and DHA.
1.35 Composition 1.34 wherein the composition comprises 0.15 weight % to 0.50 weight % of one or both of EPA and DHA.
1.36 Composition 1.35 wherein the composition comprises 0.15 weight % to 0.40 weight % of one or both of EPA and DHA.
1.37 Composition 1 or 1.1-1.36 wherein the composition comprises 0.10 weight % to 2.0 weight % EPA.
1.38 Composition 1.37 wherein the composition comprises 0.10 weight % to 1.5 weight % EPA.
1.39 Composition 1.38 wherein the composition comprises 0.10 weight % to 1.0 weight % EPA.
1.40 Composition 1.39 wherein the composition comprises 0.10 weight % to 0.80 weight % EPA.
1.41 Composition 1.40 wherein the composition comprises 0.10 weight % to 0.6 weight 0% EPA.
1.42 Composition 1.41 wherein the composition comprises 0.10 weight % to 0.40 weight % EPA.
1.43 Composition 1.42 wherein the composition comprises 0.10 weight % to 0.30 weight % EPA.
1.44 Composition 1 or 1.1-1.43 wherein the composition comprises 0.05 weight % to 2.0 weight % DHA.
1.45 Composition 1.44 wherein the composition comprises 0.05 weight % to 1.5 weight % DHA.
1.46 Composition 1.45 wherein the composition comprises 0.05 weight % to 1.0 weight % DHA.
1.47 Composition 1.46 wherein the composition comprises 0.05 weight % to 0.80 weight % DHA.
1.48 Composition 1.47 wherein the composition comprises 0.05 weight % to 0.60 weight % DHA.
1.49 Composition 1.48 wherein the composition comprises 0.05 weight % to 0.40 weight % DHA.
1.50 Composition 1.49 wherein the composition comprises 0.05 weight % to 0.20 weight % DHA.
1.51 Composition 1.50 wherein the composition comprises 0.10 weight % to 0.20 weight % DHA.
1.52 Composition 1 or 1.1-1.51 wherein the composition comprises at least 0.20 weight % fish oil.
1.53 Composition 1 or 1.1-1.52 wherein the composition comprises at least 0.50 weight % fish oil.
1.54 Composition 1 or 1.1-1.53 wherein the composition comprises at least 0.60 weight % fish oil.
1.55 Composition 1 or 1.1-1.54 wherein the composition comprises at least 0.80 weight % fish oil.
1.56 Composition 1 or 1.1-1.55 wherein the composition comprises at least 1.0 weight % fish oil.

1.57 Composition 1 or 1.1-1.56 wherein the composition comprises at least 1.2 weight % fish oil.
1.58 Composition 1 or 1.1-1.57 wherein the composition comprises at least 1.4 weight % fish oil.
1.59 Composition 1 or 1.1-1.58 wherein the composition comprises at least 1.5 weight % fish oil.
1.60 Composition 1 or 1.1-1.59 wherein the composition comprises at least 1.6 weight % fish oil.
1.61 Composition 1 or 1.1-1.60 wherein the composition comprises at least 1.8 weight % fish oil.
1.62 Composition 1 or 1.1-1.61 wherein the composition comprises at least 2.0 weight % fish oil.
1.63 Composition 1 or 1.1-1.62 wherein the composition comprises at least 2.5 weight % fish oil.
1.64 Composition 1 or 1.1-1.63 wherein the composition comprises at least 3.0 weight % fish oil.
1.65 Composition 1 or 1.1-1.64 wherein the composition comprises 0.2 weight % to 3.0 weight % fish oil.
1.66 Composition 1 or 1.1-1.65 wherein the composition comprises 0.2 weight % to 2.0 weight % fish oil.
1.67 Composition 1 or 1.1-1.66 wherein the composition comprises 0.4 weight % to 2.0 weight % fish oil.
1.68 Composition 1 or 1.1-1.67 wherein the composition comprises 0.6 weight % to 1.5 weight % fish oil.
1.69 Composition 1 or 1.1-1.68 wherein the composition comprises at least 0.10 weight % of one or more medium chain fatty acids.
1.70 Composition 1 or 1.1-1.69 wherein the composition comprises at least 0.15 weight % of one or more medium chain fatty acids.
1.71 Composition 1 or 1.1-1.70 wherein the composition comprises at least 0.20 weight % of one or more medium chain fatty acids.
1.72 Composition 1 or 1.1-1.71 wherein the composition comprises at least 0.70 weight % of one or more medium chain fatty acids.
1.73 Composition 1 or 1.1-1.72 wherein the composition comprises at least 0.90 weight % of one or more medium chain fatty acids.
1.74 Composition 1 or 1.1-1.73 wherein the composition comprises at least 1.0 weight % of one or more medium chain fatty acids.
1.75 Composition 1 or 1.1-1.74 wherein the composition comprises at least 1.3 weight % of one or more medium chain fatty acids.
1.76 Composition 1 or 1.1-1.75 wherein the composition comprises at least 1.4 v % of on or more medium chain fatty acids.
1.77 Composition 1 or 1.1-1.76 wherein the composition comprises at least 1.7 weight % of one or more medium chain fatty acids.
1.78 Composition 1 or 1.1-1.77 wherein the composition comprises at least 1.9 weight % of one or more medium chain fatty acids.
1.79 Composition 1 or 1.1-1.78 wherein the composition comprises at least 2.0 weight % of one or more medium chain fatty acids.
1.80 Composition 1 or 1.1-1.79 wherein the composition comprises at least 3.0 weight % of one or more medium chain fatty acids.
1.81 Composition 1 or 1.1-1.80 wherein the composition comprises 0.10% to 3.0 weight % of one or more medium chain fatty acids.
1.82 Composition 1 or 1.1-1.81 wherein the composition comprises 0.10% to 2.5 weight % of one or more medium chain fatty acids.
1.83 Composition 1 or 1.1-1.82 wherein the composition comprises 0.10% to 2.0 weight % of one or more medium chain fatty acids.
1.84 Composition 1 or 1.1-1.83 wherein the composition comprises 0.30% to 2.0 weight % of one or more medium chain fatty acids.
1.85 Composition 1 or 1.1-1.84 wherein the composition comprises 0.50% to 2.0 weight % of one or more medium chain fatty acids.
1.86 Composition 1.69-1.85 wherein the composition comprises one or both of capric acid, lauric acid, and myristic acid.
1.87 Composition 1 or 1.1-1.86 wherein the composition comprises at least 0.10 weight % capric acid.
1.88 Composition 1 or 1.1-1.87 wherein the composition comprises at least 0.20 weight % capric acid.
1.89 Composition 1 or 1.1-1.88 wherein the composition comprises at least 0.40 weight % capric acid.
1.90 Composition 1 or 1.1-1.89 wherein the composition comprises at least 0.60 weight % capric acid.
1.91 Composition 1 or 1.1-1.90 wherein the composition comprises at least 0.80 weight % capric acid.
1.92 Composition 1 or 1.1-1.91 wherein the composition comprises at least 1.0 weight % capric acid.
1.93 Composition 1 or 1.1-1.92 wherein the composition comprises at least 2.0 weight % capric acid.
1.94 Composition 1 or 1.1-1.93 wherein the composition comprises 0.10 weight % to 2.0 weight % capric acid.
1.95 Composition 1.94 wherein the composition comprises 0.10 weight % to 1.0 weight % capric acid.
1.96 Composition 1.95 wherein the composition comprises 0.10 weight % to 0.80 weight % capric acid.
1.97 Composition 1.96 wherein the composition comprises 0.10 weight % to 0.60 weight % capric acid.
1.98 Composition 1.97 wherein the composition comprises 0.10 weight % to 0.40 weight % capric acid.
1.99 Composition 1.98 wherein the composition comprises 0.10 weight % to 0.20 weight % capric acid.
1.100 Composition 1 or 1.1-1.99 wherein the composition comprises at least 0.10 weight % lauric acid.
1.101 Composition 1 or 1.1-1.100 wherein the composition comprises at least 0.20 weight % lauric acid.
1.102 Composition 1 or 1.1-1.101 wherein the composition comprises at least 0.40 weight % lauric acid.
1.103 Composition 1 or 1.1-1.102 wherein the composition comprises at least 0.60 weight % lauric acid.
1.104 Composition 1 or 1.1-1.103 wherein the composition comprises at least 0.80 weight % lauric acid.
1.105 Composition 1 or 1.1-1.104 wherein the composition comprises at least 1.0 weight % lauric acid.
1.106 Composition 1 or 1.1-1.105 wherein the composition comprises at least 2.0 weight % lauric acid.
1.107 Composition 1 or 1.1-1.106 wherein the composition comprises at least 3.0 weight % lauric acid.
1.108 Composition 1 or 1.1-1.107 wherein the composition comprises 0.10 weight % to 3.0 weight % lauric acid.
1.109 Composition 1.108 wherein the composition comprises 0.10 weight % to 2.0 weight % lauric acid.
1.110 Composition 1.109 wherein the composition comprises 0.10 weight % to 1.5 weight % lauric acid.
1.111 Composition 1.110 wherein the composition comprises 0.10 weight % to 1.0 weight % lauric acid.
1.112 Composition 1.111 wherein the composition comprises 0.10% to 3.0% lauric acid.
1.113 Composition 1 or 1.1-1.68 wherein the composition comprises one or more medium chain triglyceride oils.

1.114 Composition 1.113 wherein the composition comprises at least 1 weight % of one or more medium chain triglyceride oils.
1.115 Composition 1.114 wherein the composition comprises at least 2 weight % of one or more medium chain triglyceride oils.
1.116 Composition 1.115 wherein the composition comprises at least 4 weight % of one or more medium chain triglyceride oils.
1.117 Composition 1.116 wherein the composition comprises at least 6 weight % of one or more medium chain triglyceride oils.
1.118 Composition 1.117 wherein the composition comprises at least 8 weight % of one or more medium chain triglyceride oils.
1.119 Composition 1.118 wherein the composition comprises at least 10 weight % of one or more medium chain triglyceride oils.
1.120 Composition 1.119 wherein the composition comprises at least 12 weight % of one or more medium chain triglyceride oils.
1.121 Composition 1.120 wherein the composition comprises at least 15 v % of one or more medium chain triglyceride oils.
1.122 Composition 1.121 wherein the composition comprises at least 20 weight % of one or more medium chain triglyceride oils.
1.123 Composition 1.113 wherein the composition comprises 1 weight % to 20 weight % of one or more medium chain triglyceride oils.
1.124 Composition 1.123 wherein the composition comprises 1 weight % to 15 weight % of one or more medium chain triglyceride oils.
1.125 Composition 1.124 wherein the composition comprises 1 weight % to 10 weight % of one or more medium chain triglyceride oils.
1.126 Composition 1.113-1.125 wherein the one or more medium chain triglyceride oils are coconut oil or corn oil.
1.127 Composition 1 or 1.1-1.126 wherein the composition comprises 1 weight % to 10 weight % coconut oil.
1.128 Composition 1.127 wherein the composition comprises 2 weight % to 8 weight % coconut oil.
1.129 Composition 1.128 wherein the composition comprises 2 weight % to weight 5% coconut oil.
1.130 Composition 1 or 1.1-1.129 wherein the composition comprises 1 weight % to 15 weight % corn oil.
1.131 Composition 1.130 wherein the composition comprises 2 weight % to 10 weight % corn oil.
1.132 Composition 1.131 wherein the composition comprises 5 weight % to 10 weight % corn oil.
1.133 Composition 1 or 1.1-1.132 wherein the composition comprises at least 2 weight % linoleic acid (LA).
1.134 Composition 1.133 wherein the composition comprises at least 3 weight % linoleic acid (LA).
1.135 Composition 1.134 wherein the composition comprises at least 4 weight % linoleic acid (LA).
1.136 Composition 1.135 wherein the composition comprises at least 5 weight % linoleic acid (LA).
1.137 Composition 1.136 wherein the composition comprises at least 8 weight % linoleic acid (LA).
1.138 Composition 1.137 wherein the composition comprises at least 10 weight % linoleic acid (LA).
1.139 Composition 1 or 1.1-1.138 wherein the composition weight comprises 2 weight % to 10 weight % linoleic acid.
1.140 Composition 1.139 wherein the composition comprises 3 weight % to 8 weight % linoleic acid.
1.141 Composition 1.140 wherein the composition comprises 4 weight % to 6 weight % linoleic acid.
1.142 Composition 1.141 wherein the composition comprises 4 weight % to 5 weight % linoleic acid.
1.143 Composition 1 or 1.1-1.142 wherein the composition comprises at least 1.5 weight % α-linolenic acid, e.g., from 1.5 weight % to 10 weight %, e.g, from 1.5 weight % to 8 weight %, e.g., from 1.5 weight % to 5 weight %, e.g., from 1.5 to 3 weight %.
1.144 Composition 1 or 1.1-1.143 wherein the composition comprises arachidonic acid.
1.145 Composition 1 or 1.1-1.144 wherein the composition comprises a ratio of eicosapentaenoic acid to arachidonic acid of 1.2:1 or greater.
1.146 Composition 1.145 wherein the composition comprises a ratio of eicosapentaenoic acid to arachidonic acid of 1.3:1 or greater.
1.147 Composition 1.146 wherein the composition comprises a ratio of eicosapentaenoic acid to arachidonic acid of 1.5:1 or greater.
1.148 Composition 1.147 wherein the composition comprises a ratio of eicosapentaenoic acid to arachidonic acid of 2:1 or greater.
1.149 Composition 1.148 wherein the composition comprises a ratio of eicosapentaenoic acid to arachidonic acid of 3:1 or greater.
1.150 Composition 1.149 wherein the composition comprises a ratio of eicosapentaenoic acid to arachidonic acid of 3.5:1 or greater.
1.151 Composition 1.150 wherein the composition comprises a ratio of eicosapentaenoic acid to arachidonic acid of 3.8:1 or greater.
1.152 Composition 1.151 wherein the composition comprises a ratio of eicosapentaenoic acid to arachidonic acid of 4:1 or greater.
1.153 Composition 1 or 1.1-1.152 wherein the composition comprises 0.01 weight % to 0.5 weight % arachidonic acid.
1.154 Composition 1.153 wherein the composition comprises 0.01 weight % to 0.1 weight % arachidonic acid.
1.155 Composition 1.154 wherein the composition comprises 0.01 weight % to 0.08 weight % arachidonic acid.
1.156 Composition 1.155 wherein the composition comprises 0.02 weight % to 0.07 weight % arachidonic acid.
1.157 Composition 1.156 wherein the composition comprises 0.03 weight % to 0.07 weight % arachidonic acid.
1.158 Composition 1.157 wherein the composition comprises 0.04 weight % to 0.06 weight % arachidonic acid.
1.159 Composition 1.158 wherein the composition comprises 0.06 weight % arachidonic acid.
1.160 Composition 1 or 1.1-1.159 wherein the composition is a dog food.
1.161 Composition 1.160 wherein the composition comprises one or more of protein, fiber, and nutritional balancing agents.
1.162 Composition 1.161 wherein the composition comprises at least 10 weight % protein, at least 10 weight % fat, and at least 0.5 weight % crude fiber.
1.163 Composition 1.162 wherein the composition comprises at least 15 weight % fat and at least 1.0 weight % crude fiber.

1.164 Composition 1.158-1.163 wherein the composition comprises at least 0.50 weight % calcium, 0.10 weight % phosphorus, and 0.1 weight % sodium.
1.165 Composition 1.164 wherein the composition comprises at least 0.70 weight % calcium, 0.20 weight % phosphorus, and 0.2 weight % sodium.
1.166 Composition 1.158-1.165 wherein the composition comprises at least 1.0% alpha-linoleic acid (α-LA).
1.167 Method 1.166 wherein the composition comprises at least 1.0 weight % alpha-linoleic acid (α-LA).
1.168 Composition 1.167 wherein the composition comprises at least 1.5 weight % alpha-linoleic acid (α-LA).
1.169 Composition 1 or 1.1-1.168 wherein the composition comprises at least 4.0 weight % of one or more saturated fatty acids.
1.170 Composition 1.169 wherein the composition comprises at least 4.5 weight % of one or more saturated fatty acids.
1.171 Composition 1 or 1.1-1.170 wherein the composition comprises at least 5.0 weight % or one or more monounsaturated fatty acids.
1.172 Composition 1 or 1.1-1.171 wherein the composition comprises at least 4.0 weight % of one or more polyunsaturated fatty acids.
1.173 Composition 1 or 1.1-1.172 wherein the composition comprises at least 3.0 weight % of omega-6 fatty acids (n-6 fatty acids) and at least 1.0 weight % of omega-3 fatty acids (n-3 fatty acids).
1.174 Composition 1 or 1.1-1.159 wherein the composition is a dog treat.
1.175 Composition 1 or 1.1-1.174 wherein the composition comprises one or more renal drugs.
1.176 Composition 1 or 1.1-1.175 wherein the composition is administered in conjunction with one or more renal drugs.

In yet another embodiment provided is a composition comprising L-carnitine and one or both of eicosapentaenoic acid (EPA) and docosahexaenoic acid (DHA) in an amount effective for the treatment or prophylaxis of kidney disease in a dog in need thereof (Composition 2).

Further provided is Composition 2 as follows:
2.1 Composition 2 wherein the composition comprises at least 100 ppm L-carnitine.
2.2 Composition 2 or 2.1 wherein the composition comprises at least 200 ppm L-carnitine.
2.3 Composition 2, 2.1, or 2.2 wherein the composition comprises at least 300 ppm L-carnitine.
2.4 Composition 2 or 2.1-2.3 wherein the composition comprises 100 ppm to 1500 ppm L-carnitine.
2.5 Composition 2 or 2.1-2.4 wherein the composition comprises 200 ppm to 1500 ppm L-carnitine.
2.6 Composition 2 or 2.1-2.5 wherein the composition comprises 200 ppm to 1200 ppm L-carnitine.
2.7 Composition 2 or 2.1-2.6 wherein the composition comprises 200 ppm to 1000 ppm L-carnitine.
2.8 Composition 2 or 2.1-2.7 wherein the composition comprises 200 ppm to 800 ppm L-carnitine.
2.9 Composition 2 or 2.1-2.8 wherein the composition comprises 200 ppm to 700 ppm L-carnitine.
2.10 Composition 2 or 2.1-2.9 wherein the composition comprises 300 ppm to 600 ppm L-carnitine.
2.11 Composition 2 or 2.1-2.10 wherein the composition comprises 300 ppm L-carnitine.
2.12 Composition 2 or 2.1-2.11 wherein the composition comprises at least 0.10 weight % of one or both of EPA and DHA.
2.13 Composition 2 or 2.1-2.12 wherein the composition comprises at least 0.15 weight % of one or both of EPA and DHA.
2.14 Composition 2 or 2.1-2.13 wherein the composition comprises at least 0.20 weight % of one or both of EPA and DHA.
2.15 Composition 2 or 2.1-2.14 wherein the composition comprises at least 0.30 weight % of one or both of EPA and DHA.
2.16 Composition 2 or 2.1-2.15 wherein the composition comprises at least 0.35 weight % of one or both of EPA and DHA.
2.17 Composition 2 or 2.1-2.16 wherein the composition comprises at least 0.40 weight % of one or both of EPA and DHA.
2.18 Composition 2 or 2.1-2.17 wherein the composition comprises at least 0.50 weight % of one or both of EPA and DHA.
2.19 Composition 2 or 2.1-2.11 wherein the composition comprises at least 0.1 weight 0% of EPA.
2.20 Composition 2.19 wherein the composition comprises at least 0.15 weight % of EPA.
2.21 Composition 2.20 wherein the composition comprises at least 0.20 weight % of EPA.
2.22 Composition 2.21 wherein the composition comprises at least 0.25 weight % of EPA.
2.23 Composition 2.22 wherein the composition comprises at least 0.30 weight % of EPA.
2.24 Composition 2, 2.1-2.11, or 2.12-2.23 wherein the composition comprises at least 0.05 weight % of DHA.
2.25 Composition 2.24 wherein the composition comprises at least 0.10 weight % of DHA.
2.26 Composition 2.25 wherein the composition comprises at least 0.15 weight % of DHA.
2.27 Composition 2.26 wherein the composition comprises at least 0.2 weight 0% of DHA.
2.28 Composition 2 or 2.1-2.27 wherein the composition comprises at least 0.10 weight % EPA and at least 0.05 weight % DHA.
2.29 Composition 2.28 wherein the composition comprises at least 0.10 weight % EPA and at least 0.07 weight % DHA.
2.30 Composition 2.29 wherein the composition comprises at least 0.20 weight % EPA and at least 0.15 weight % DHA.
2.31 Composition 2.30 wherein the composition comprises at least 0.23 weight % EPA and at least 0.16 weight % DHA.
2.32 Composition 2 or 2.1-2.31 wherein the composition comprises 0.10 weight % to 2.0 weight % of one or both of EPA and DHA.
2.33 Composition 2.32 wherein the composition comprises 0.10 weight % to 1.5 weight % of one or both of EPA and DHA.
2.34 Composition 2.33 wherein the composition comprises 0.15 weight % to 1.0 weight % of one or both of EPA and DHA.
2.35 Composition 2.34 wherein the composition comprises 0.15 weight % to 0.50 weight % of one or both of EPA and DHA.
2.36 Composition 2.35 wherein the composition comprises 0.15 weight % to 0.40 weight % of one or both of EPA and DHA.
2.37 Composition 2 or 2.1-2.36 wherein the composition comprises 0.10 weight % to 2.0 weight % EPA.
2.38 Composition 2.37 wherein the composition comprises 0.10 weight % to 1.5 weight % EPA.

2.39 Composition 2.38 wherein the composition comprises 0.10 weight % to 1.0 weight % EPA.
2.40 Composition 2.39 wherein the composition comprises 0.10 weight % to 0.80 weight % EPA.
2.41 Composition 2.40 wherein the composition comprises 0.10 weight % to 0.60 weight % EPA.
2.42 Composition 2.41 wherein the composition comprises 0.10 weight % to 0.40 weight % EPA.
2.43 Composition 2.42 wherein the composition comprises 0.10 weight % to 0.30 weight % EPA.
2.44 Composition 2 or 2.1-2.43 wherein the composition comprises 0.05 weight % to 2.0 weight % DHA.
2.45 Composition 2.44 wherein the composition comprises 0.05 weight % to 1.5 weight % DHA.
2.46 Composition 2.45 wherein the composition comprises 0.05 weight % to 1.0 weight % DHA.
2.47 Composition 2.46 wherein the composition comprises 0.05 weight % to 0.80 weight % DHA.
2.48 Composition 2.47 wherein the composition comprises 0.05 weight % to 0.60 weight % DHA.
2.49 Composition 2.48 wherein the composition comprises 0.05 weight % to 0.40 weight % DHA.
2.50 Composition 2.49 wherein the composition comprises 0.05 weight % to 0.20 weight % DHA.
2.51 Composition 2.50 wherein the composition comprises 0.10 weight % to 0.20 weight % DHA.
2.52 Composition 2 or 2.1-2.51 wherein the composition comprises at least 0.20 weight % fish oil.
2.53 Composition 2 or 2.1-2.52 wherein the composition comprises at least 0.50 weight % fish oil.
2.54 Composition 2 or 2.1-2.53 wherein the composition comprises at least 0.60 weight % fish oil.
2.55 Composition 2 or 2.1-2.54 wherein the composition comprises at least 0.80 weight % fish oil.
2.56 Composition 2 or 2.1-2.55 wherein the composition comprises at least 1.0 weight % fish oil.
2.57 Composition 2 or 2.1-2.56 wherein the composition comprises at least 1.2 weight % fish oil.
2.58 Composition 2 or 2.1-2.57 wherein the composition comprises at least 1.4 weight % fish oil.
2.59 Composition 2 or 2.1-2.58 wherein the composition comprises at least 1.5 weight % fish oil.
2.60 Composition 2 or 2.1-2.59 wherein the composition comprises at least 1.6 weight % fish oil.
2.61 Composition 2 or 2.1-2.60 wherein the composition comprises at least 1.8 weight % fish oil.
2.62 Composition 2 or 2.1-2.61 wherein the composition comprises at least 2.0 weight % fish oil.
2.63 Composition 2 or 2.1-2.62 wherein the composition comprises at least 2.5 weight % fish oil.
2.64 Composition 2 or 2.1-2.63 wherein the composition comprises at least 3.0 weight % fish oil.
2.65 Composition 2 or 2.1-2.64 wherein the composition comprises 0.2 weight % to 3.0 weight % fish oil.
2.66 Composition 2 or 2.1-2.65 wherein the composition comprises 0.2 weight % to 2.0 weight % fish oil.
2.67 Composition 2 or 2.1-2.66 wherein the composition comprises 0.4 weight % to 2.0 weight % fish oil.
2.68 Composition 2 or 2.1-2.67 wherein the composition comprises 0.6 weight % to 1.5 weight % fish oil.
2.69 Composition 2 or 2.1-1.68 wherein the composition comprises at least 0.10 weight % of one or more medium chain fatty acids.
2.70 Composition 2 or 2.1-2.69 wherein the composition comprises at least 0.15 weight % of one or more medium chain fatty acids.
2.71 Composition 2 or 2.1-2.70 wherein the composition comprises at least 0.20 weight % of one or more medium chain fatty acids.
2.72 Composition 2 or 2.1-2.71 wherein the composition comprises at least 0.70 weight % of one or more medium chain fatty acids.
2.73 Composition 2 or 2.1-2.72 wherein the composition comprises at least 0.90 weight % of one or more medium chain fatty acids.
2.74 Composition 2 or 2.1-2.73 wherein the composition comprises at least 1.0 weight % of one or more medium chain fatty acids.
2.75 Composition 2 or 2.1-2.74 wherein the composition comprises at least 1.3 weight % of one or more medium chain fatty acids.
2.76 Composition 2 or 2.1-2.75 wherein the composition comprises at least 1.4 weight % of one or more medium chain fatty acids.
2.77 Composition 2 or 2.1-2.76 wherein the composition comprises at least 1.7 weight % of one or more medium chain fatty acids.
2.78 Composition 2 or 2.1-2.77 wherein the composition comprises at least 1.9 weight % of one or more medium chain fatty acids.
2.79 Composition 2 or 2.1-2.78 wherein the composition comprises at least 2.0 weight % of one or more medium chain fatty acids.
2.80 Composition 2 or 2.1-2.79 wherein the composition comprises at least 3.0 weight % of one or more medium chain fatty acids.
2.81 Composition 2 or 2.1-2.80 wherein the composition comprises 0.10 weight % to 3.0 weight % of one or more medium chain fatty acids.
2.82 Composition 2 or 2.1-2.81 wherein the composition comprises 0.10 weight % to 2.5 weight % of one or more medium chain fatty acids.
2.83 Composition 2 or 2.1-2.82 wherein the composition comprises 0.10 weight % to 2.0 weight % of one or more medium chain fatty acids.
2.84 Composition 2 or 2.1-2.83 wherein the composition comprises 0.30 weight % to 2.0 weight % of one or more medium chain fatty acids.
2.85 Composition 2 or 2.1-2.84 wherein the composition comprises 0.50 weight % to 2.0 weight % of one or more medium chain fatty acids.
2.86 Composition 2.69-2.85 wherein the composition comprises one or both of capric acid, lauric acid, and myristic acid.
2.87 Composition 2 or 2.1-2.86 wherein the composition comprises at least 0.10 weight % capric acid.
2.88 Composition 2 or 2.1-2.87 wherein the composition comprises at least 0.20 weight % capric acid.
2.89 Composition 2 or 2.1-2.88 wherein the composition comprises at least 0.40 weight % capric acid.
2.90 Composition 2 or 2.1-2.89 wherein the composition comprises at least 0.60 weight % capric acid.
2.91 Composition 2 or 21-2.90 wherein the composition comprises at least 0.80 weight % capric acid.
2.92 Composition 2 or 2.1-2.91 wherein the composition comprises at least 1.0 weight % capric acid.
2.93 Composition 2 or 2.1-2.92 wherein the composition comprises at least 2.0 weight % capric acid.
2.94 Composition 2 or 2.1-2.93 wherein the composition comprises 0.10 weight % to 2.0 weight % capric acid.
2.95 Composition 2.94 wherein the composition comprises 0.10 weight % to 1.0 weight % capric acid.

2.96 Composition 2.95 wherein the composition comprises 0.10 weight % to 0.80 weight % capric acid.
2.97 Composition 2.96 wherein the composition comprises 0.10 weight % to 0.60 weight % capric acid.
2.98 Composition 2.97 wherein the composition comprises 0.10 weight % to 0.40 weight % capric acid.
2.99 Composition 2.98 wherein the composition comprises 0.10 weight % to 0.20 weight % capric acid.
2.100 Composition 2 or 2.1-2.99 wherein the composition comprises at least 0.10 weight % lauric acid.
2.101 Composition 2 or 2.1-2.100 wherein the composition comprises at least 0.20 weight % lauric acid.
2.102 Composition 2 or 2.1-2.101 wherein the composition comprises at least 0.40 weight % lauric acid.
2.103 Composition 2 or 2.69-2.102 wherein the composition comprises at least 0.60 weight % lauric acid.
2.104 Composition 2 or 2.1-2.103 wherein the composition comprises at least 0.80 weight % lauric acid.
2.105 Composition 2 or 2.1-2.104 wherein the composition comprises at least 1.0 weight % lauric acid.
2.106 Composition 2 or 2.1-2.105 wherein the composition comprises at least 2.0 weight % lauric acid.
2.107 Composition 2 or 2.1-2.106 wherein the composition comprises at least 3.0 weight % lauric acid.
2.108 Composition 2 or 2.1-2.99 wherein the composition comprises 0.10% to 3.0% lauric acid.
2.109 Composition 2.108 wherein the composition comprises 0.10 weight % to 2.0 weight % lauric acid.
2.110 Composition 2.109 wherein the composition comprises 0.10 weight % to 1.5 weight % lauric acid.
2.111 Composition 2.110 wherein the composition comprises 0.10 weight % to 1.0 weight % lauric acid.
2.112 Composition 2.111 wherein the composition comprises 0.10 weight % to 3.0 weight % lauric acid.
2.113 Composition 2 or 2.1-2.68 wherein the composition comprises one or more medium chain triglyceride oils.
2.114 Composition 2.113 wherein the composition comprises at least 1 weight % of one or more medium chain triglyceride oils.
2.115 Composition 2.114 wherein the composition comprises at least 2 weight % of one or more medium chain triglyceride oils.
2.116 Composition 2.115 wherein the composition comprises at least 4 weight % of one or more medium chain triglyceride oils.
2.117 Composition 2.116 wherein the composition comprises at least 6 weight % of one or more medium chain triglyceride oils.
2.118 Composition 2.117 wherein the composition comprises at least 8 weight % of one or more medium chain triglyceride oils.
2.119 Composition 2.118 wherein the composition comprises at least 10 weight % of one or more medium chain triglyceride oils.
2.120 Composition 2.119 wherein the composition comprises at least 12 weight % of one or more medium chain triglyceride oils.
2.121 Composition 2.120 wherein the composition comprises at least 15 weight % of one or more medium chain triglyceride oils.
2.122 Composition 2.121 wherein the composition comprises at least 20 weight % of one or more medium chain triglyceride oils.
2.123 Composition 2.122 wherein the composition comprises 1 weight % to 20 weight % of one or more medium chain triglyceride oils.
2.124 Composition 2.123 wherein the composition comprises 1 weight % to 15 weight % of one or more medium chain triglyceride oils.
2.125 Composition 2.124 wherein the composition comprises 1 weight % to 10 weight % of one or more medium chain triglyceride oils.
2.126 Composition 2.113-1.125 wherein the one or more medium chain triglyceride oils are coconut oil or corn oil.
2.127 Composition 2 or 2.1-2.126 wherein the composition comprises 1 weight % to 10 weight % coconut oil.
2.128 Composition 2.127 wherein the composition comprises 2 weight % to 8 weight % coconut oil.
2.129 Composition 2.128 wherein the composition comprises 2 weight % to 5 weight % coconut oil.
2.130 Composition 2.1-2.129 wherein the composition comprises 1 weight % to 15 weight % corn oil.
2.131 Composition 2.130 wherein the composition comprises 2 weight % to 10 weight % corn oil.
2.132 Composition 2.131 wherein the composition comprises 5 weight % to 10 weight % corn oil.
2.133 Composition 2 or 2.1-2.132 wherein the composition comprises at least 2 weight % linoleic acid (LA).
2.134 Composition 2.133 wherein the composition comprises at least 3 weight % linoleic acid (LA).
2.135 Composition 2.134 wherein the composition comprises at least 4 weight % linoleic acid (LA).
2.136 Composition 2.135 wherein the composition comprises at least 5 weight % linoleic acid (LA).
2.137 Composition 2.136 wherein the composition comprises at least 8 weight % linoleic acid (LA).
2.138 Composition 2.136 wherein the composition comprises at least 10 weight % linoleic acid (LA).
2.139 Composition 2 or 2.1-2.138 wherein the composition comprises 2% weight to 10 weight % linoleic acid.
2.140 Composition 2.139 wherein the composition comprises 3 weight % to 8 weight % linoleic acid.
2.141 Composition 2.140 wherein the composition comprises 4 weight % to 6 weight % linoleic acid.
2.142 Composition 2.141 wherein the composition comprises 4 weight % to 5 weight % linoleic acid.
2.143 Composition 2 or 2.1-2.142 wherein the composition comprises at least 1.5 weight % α-linolenic acid, e.g., from 1.5 weight % to 10 weight %, e.g, from 1.5 weight % to 8 weight %, e.g., from 1.5 weight % to 5 weight %, e.g., from 1.5 to 3 weight %.
2.144 Composition 2 or 2.1-2.143 wherein the composition comprises arachidonic acid.
2.145 Composition 2 or 2.1-2.144 wherein the composition comprises a ratio of eicosapentaenoic acid to arachidonic acid of 1.2:1 or greater.
2.146 Composition 2.145 wherein the composition comprises a ratio of eicosapentaenoic acid to arachidonic acid of 1.3:1 or greater.
2.147 Composition 2.146 wherein the composition comprises a ratio of eicosapentaenoic acid to arachidonic acid of 1.5:1 or greater.
2.148 Composition 2.147 wherein the composition comprises a ratio of eicosapentaenoic acid to arachidonic acid of 2:1 or greater.
2.149 Composition 2.148 wherein the composition comprises a ratio of eicosapentaenoic acid to arachidonic acid of 3:1 or greater.
2.150 Composition 2.149 wherein the composition comprises a ratio of eicosapentaenoic acid to arachidonic acid of 3.5:1 or greater.

2.151 Composition 2.150 wherein the composition comprises a ratio of eicosapentaenoic acid to arachidonic acid of 3.8:1 or greater.
2.152 Composition 2.151 wherein the composition comprises a ratio of eicosapentaenoic acid to arachidonic acid of 4:1 or greater.
2.153 Composition 2 or 2.1-2.152 wherein the composition comprises 0.01 weight % to 0.5 weight % arachidonic acid.
2.154 Composition 2.153 wherein the composition comprises 0.01 weight % to 0.1 weight % arachidonic acid.
2.155 Composition 2.154 wherein the composition comprises 0.01 weight % to 0.08 weight % arachidonic acid.
2.156 Composition 2.155 wherein the composition comprises 0.02 weight % to 0.07 weight % arachidonic acid.
2.157 Composition 2.156 wherein the composition comprises 0.03 weight % to 0.07 weight % arachidonic acid.
2.158 Composition 2.157 wherein the composition comprises 0.04 weight % to 0.06 weight % arachidonic acid.
2.159 Composition 2.158 wherein the composition comprises 0.06 weight % arachidonic acid.
2.160 Composition 2 or 2.1-2.159 wherein the composition is a dog food.
2.161 Composition 2.160 wherein the composition comprises one or more of protein, fiber, and nutritional balancing agents.
2.162 Composition 2.161 wherein the composition comprises at least 10 weight % protein, at least 10 weight % fat, and at least 0.5 weight % crude fiber.
2.163 Composition 2.162 wherein the composition comprises at least 15 weight % fat and at least 1.0 weight % crude fiber.
2.164 Composition 2.158-2.163 wherein the composition comprises at least 0.50 weight % calcium, 0.10 weight % phosphorus, and 0.1 weight % sodium.
2.165 Composition 2.164 wherein the composition comprises at least 0.70 weight % calcium, 0.20 weight % phosphorus, and 0.2 weight % sodium.
2.166 Composition 2.158-2.165 wherein the composition comprises at least 1.0 weight % alpha-linoleic acid (α-LA).
2.167 Composition 2.166 wherein the composition comprises at least 1.0 weight % alpha-linoleic acid (α-LA).
2.168 Composition 2.167 wherein the composition comprises at least 1.5 weight % alpha-linoleic acid (α-LA).
2.169 Composition 2 or 2.1-2.168 wherein the composition comprises at least 4.0 weight % of one or more saturated fatty acids.
2.170 Composition 2.169 wherein the composition comprises at least 4.5 weight % of one or more saturated fatty acids.
2.171 Composition 2 or 2.1-2.170 wherein the composition comprises at least 5.0 weight % or one or more monounsaturated fatty acids.
2.172 Composition 2 or 2.1-2.171 wherein the composition comprises at least 4.0 weight % of one or more polyunsaturated fatty acids.
2.173 Composition 2 or 2.1-2.172 wherein the composition comprises at least 3.0 weight % of omega-6 fatty acids (n-6 fatty acids) and at least 1.0% of omega-3 fatty acids (n-3 fatty acids).
2.174 Composition 2 or 2.1-2.159 wherein the composition is a dog treat.
2.175 Composition 2 or 2.1-2.174 wherein the composition comprises one or more renal drugs.
2.176 Composition 2 or 2.1-2.175 wherein the composition is administered in conjunction with one or more renal drugs.

A composition of the present disclosure, e.g., Composition 1, e.g., 1.1-1.176 or, e.g., Composition 2, e.g., 2.1-2.176, is administered to a dog by using any suitable method, preferably by feeding the composition to the dog.

A composition of the present disclosure, e.g., Composition 1, e.g., 1.1-1.176 or, e.g., Composition 2, e.g., 2.1-2.176, may be administered orally using any suitable form for oral administration, e.g., tablets, pills, suspensions, solutions (possibly admixed with drinking water), emulsions, capsules, powders, syrups, and food compositions. In a preferred embodiment, the composition components and the food ingredients are admixed during manufacture process used to prepare a composition suitable for administration in the form of a dog food for consumption by the dog.

A method according to the present disclosure, e.g., Method 1, e.g., 1.1-1.176, or, e.g., Method 2, e.g., 2.1-2.176, may be accomplished by administering a composition to the dog in various forms. For example, one or more composition components and food ingredients are in separate containers and admixed just prior to administration. In another embodiment, one or more of the composition components are admixed with the food ingredients during manufacture and the remaining composition components admixed with such food ingredients just prior to administration. In a further embodiment, the composition is a component of a pour-on formulation (preferably containing vitamins and minerals) that is applied to food ingredients prior to administration. In another, the composition is admixed with one or more food ingredients and such admixture is mixed with other food ingredients before administration. In a further embodiment, the composition is coated onto the food ingredients during the manufacturing process or after the food composition is manufactured. In another, the composition is administered orally and the food composition is fed to the animal.

In yet another embodiment provided is use of a composition comprising L-carnitine and one or both of eicosapentaenoic acid (EPA) and docosahexaenoic acid (DHA) in an amount effective to improve kidney function in a dog in need thereof (Use 1).

In yet another embodiment provided is use of a composition comprising L-carnitine, one or both of eicosapentaenoic acid (EPA) and docosahexaenoic acid (DHA), and one or more medium chain fatty acids in an amount effective to improve kidney function in a dog in need thereof (Use 2).

In yet another embodiment provided is use of a composition comprising L-carnitine, one or both of eicosapentaenoic acid (EPA) and docosahexaenoic acid (DHA), one or more medium chain fatty acids, and a ratio of eicosapentaenoic acid to arachidonic acid in an amount effective to improve kidney function in a dog in need thereof (Use 3).

In yet another embodiment provided is use of Composition 1, e.g., 1.1-1.176, or Composition 2, e.g., 2.1-2.176, to improve kidney function in a dog in need thereof (Use 4).

In yet another embodiment provided is use of a composition comprising L-carnitine and one or both of eicosapentaenoic acid (EPA) and docosahexaenoic acid (DHA) in an amount effective for the treatment or prophylaxis of kidney disease in a dog in need thereof (Use 5).

In yet another embodiment provided is use of a composition comprising L-carnitine, one or both of eicosapentaenoic acid (EPA) and docosahexaenoic acid (DHA), and one or more medium chain fatty acids in an amount effective for the treatment or prophylaxis of kidney disease in a dog in need thereof (Use 6).

In yet another embodiment provided is use of a composition comprising L-carnitine, one or both of eicosapentaenoic acid (EPA) and docosahexaenoic acid (DHA), one or more medium chain fatty acids, and a ratio of eicosapentaenoic acid to arachidonic acid in an amount effective for the treatment or prophylaxis of kidney disease in a dog in need thereof (Use 7).

In yet another embodiment provided is use of Composition 1, e.g., 1.1-1.176, or Composition 2, e.g., 2.1-2.176, for the treatment or prophylaxis of kidney disease in a dog in need thereof (Use 8).

In yet another embodiment provided is use of L-carnitine and one or both of eicosapentaenoic acid (EPA) and docosahexaenoic acid (DHA) in the manufacture of a dog food composition for use in a method according to Method 1, e.g., 1.1-1.176 or Method 2, e.g., 2.1-2.176, or Uses 1-8.

In yet another embodiment provided is use of L-carnitine, one or both of eicosapentaenoic acid (EPA) and docosahexaenoic acid (DHA), and one or more medium chain fatty acids in the manufacture of a dog food composition for use in a method according to Method 1, e.g., 1.1-1.176 or Method 2. e.g., 2.1-2.176, or Uses 1-8.

In yet another embodiment provided is use of L-carnitine, one or both of eicosapentaenoic acid (EPA) and docosahexaenoic acid (DHA), one or more medium chain fatty acids, and a ratio of eicosapentaenoic acid to arachidonic acid in the manufacture of a dog food composition for use in a method according to Method 1, e.g., 1.1-1.176 or Method 2, e.g., 2.1-2.176, or Uses 1-8.

EXAMPLES

Example 1

Forty one healthy Beagle dogs with mean age of 9.9 years (range 3.1 to 14.8 years) are included in this study. Equal numbers of females (n=21; ovariohysterectomized) and males (n=20; neutered) are randomized to 3 study groups. Initial body weight, mean±SEM, is 12.4±0.4 kg. Exclusion criteria included the inability to eat dry food and/or any diagnosed disease condition. The criterion for removal from the study is development of any condition whereby removal would benefit the animal.

Foods

All foods contain similar concentrations (within analytical variance of targets) of protein, fat, calcium, phosphorus, and sodium, and were isocaloric. The control food lacks appreciable quantities of long chain EPA and DHA, and medium-chain capric [10:0], lauric [12:0], and myristic [14:0] fatty acids (FA). Control food is richest in palmitic [16:0] and stearic [18:0] FA. Food Test 1 is richer in EPA and DHA than control food, but comparable in medium-chain FA content. Food Test 2 contains increased concentrations of EPA and DHA, as well as increased concentrations of medium-chain FA, and linoleic [LA, 18:2 (n-6)] and α-linolenic [αLA, 18:3 (n-3)] FA. Food Test 2 also contains the least amounts of palmitic, stearic, and AA FA. All foods have relatively the same (n-6) to (n-3) FA ratio, which is approximately 2.3:1.

In summary, the dietary treatments are Control Food (no enhancement of n-6 or n-3 fatty acids or carnitine), Food Test 1 (0.17% sum of EPA and DHA and 300 ppm carnitine), and Food Test 2 0.39% EPA and DHA, added carnitine, added MCT oil and added n-6 fatty acids). For complete analyticals see Table 4.

Results

Feeding this mix of nutrients results in an increase in creatine as well as an increase in glomerular filtration rate (GFR) and a decrease in plasma concentration of symmetrical dimethyl arginine (SDMA).

TABLE 1

Least Squared Means of Glomerular Filtration Rate (ml/kg/min)

| Diet | LSMEAN | Standard Error |
|---|---|---|
| Control | $3.30^a$ | 0.247 |
| Test #2 | $4.08^b$ | 0.325 |
| Test #1 | $3.46^{a,b}$ | 0.310 |

TABLE 2

Plasma concentrations of creatine (arbitrary units based on metabolomics analysis)

| Diet | LSMEAN | Standard Error |
|---|---|---|
| Control | $0.64^a$ | 0.127 |
| Test #2 | $1.02^b$ | 0.180 |
| Test #1 | $0.87a,b^b$ | 0.161 |

TABLE 3

Plasma concentrations of SDMA (symmetrical dimethyl arginine a marker of renal function)

| Diet | LSMEAN | Standard Error |
|---|---|---|
| Control | $7.37^a$ | 0.39 |
| Test #2 | $5.52^b$ | 0.39 |
| Test #1 | $6.46^{a,b}$ | 0.42 |

Thus, the blend of ingredients of carnitine, EPA and DHA, linoleic acid, and medium chain fatty acids (c:10, c:12 and c:14 all unsaturated) effect GFR, creatine, and SDMA. As GFR elevation and SDMA decline are both signs of a positive benefit for renal function we conclude that Food Test 2 is beneficial for dogs with declining renal function. In addition, as GFR and creatine are significantly correlated, the effect on GFR may be mediated at least in part through the change in creatine.

Food Test 2 also contains the least amount of AA FA. Food Test 2 results in a reduction in circulating AA. The mean change in circulating AA over the time of the study is that the Control Food results in a significant increase in circulating AA (7.28), Test Food 1 results in an insignificant increase in circulating AA (1.49), and Test Food 2 results in a significant decline in circulating AA (−11.22). Reduction in circulating AA may (working with the increased EPA and DHA) reduce inflammation in the kidney leading to improvement in the reported markers of renal function.

TABLE 4

Food composition of control food and two dietary treatment foods[a]

|  | Control Food | Increased (n-3) FA Food Test 1 | Increased (n-3&6) FA Food Test 2 |
| --- | --- | --- | --- |
| Added Fish Oil, % | 0 | 0.6 | 1.5 |
| Added L-carnitine, mg/kg | 0 | 300 | 300 |
| Added Coconut and Corn Oils, (+, −) | − | − | + |
| Moisture | 6.88 | 7.86 | 7.58 |
| Protein | 13.66 | 14.12 | 14.09 |
| Fat | 18.15 | 17.89 | 18.32 |
| Atwater Energy[b] (kcal/kg) | 3,960 | 3,921 | 3,959 |
| Ash | 3.9 | 4.38 | 3.97 |
| Crude Fiber | 2.0 | 1.3 | 1.5 |
| Calcium | 0.70 | 0.75 | 0.72 |
| Phosphorus | 0.28 | 0.31 | 0.29 |
| Sodium | 0.2 | 0.2 | 0.2 |
| Capric acid [10:0] | 0.0 | 0.01 | 0.12 |
| Lauric acid [12:0] | 0.01 | 0.01 | 0.87 |
| Myristic acid [14:0] | 0.17 | 0.18 | 0.46 |
| Palmitic acid [16:0] | 3.6 | 3.45 | 2.26 |
| Stearic acid [18:0] | 1.67 | 1.53 | 0.76 |
| Arachidic acid [20:0] | 0.03 | 0.03 | 0.04 |
| LA [18:2 (n-6)] | 3.07 | 3.09 | 4.61 |
| αLA [18:3 (n-3)] | 1.27 | 1.35 | 1.63 |
| AA [20:4 (n-6)] | 0.08 | 0.08 | 0.06 |
| EPA [20:5 (n-3)] | 0.01 | 0.10 | 0.23 |
| DHA [22:6 (n-3)] | 0.00 | 0.07 | 0.16 |
| Σ SFA[c] | 5.56 | 5.40 | 4.70 |
| Σ MUFA[d] | 6.81 | 6.21 | 5.26 |
| Σ PUFA[e] | 4.52 | 4.50 | 6.65 |
| Σ (n-6) FA[f] | 3.22 | 3.15 | 4.59 |
| Σ (n-3) FA[g] | 1.30 | 1.49 | 2.06 |
| (n-6):(n-3) ratio | 2.48 | 2.11 | 2.23 |

[a]All analytical values are expressed as percentage of food as fed, unless otherwise indicated.
[b]Calculated from analyticals using modified Atwater numbers (kcal/g of 3.5 for protein, 8.5 for fat and 3.5 for nitrogen free extract)
[c]Sum of the saturated fatty acids: 8:0 + 10:0 + 11:0 + 12:0 + 14:0 + 15:0 + 16:0 + 17:0 + 18:0 + 20:0 + 22:0 + 24:0.
[d]SUM of the monounsaturated fatty acids: 14:1 + 15:1 + 16:1 + 17:1 + 18:1 + 20:1 + 22:1 + 24:1.
[e]Sum of the polyunsaturated fatty acids: 18:2(n-6) + 18:3(n-6) + 18:3(n-3) + 18:4(n-3) + 20:2(n-6) + 20:3(n-6) + 20:3(n-3) + 20:4(n-6) + 20:4(n-3) + 20:5(n-3) + 21:5(n-3) + 22:2(n-6) + 22:4(n-6) + 22:5(n-6) + 22:5(n-3) + 22:6(n-3).
[f]Sum of the (n-6) fatty acids.
[g]Sum of the (n-3) fatty acids.

I claim:

1. A method for improving kidney function in a dog in need thereof comprising administering to the dog a composition comprising an effective amount of L-carnitine and both of eicosapentaenoic acid (EPA) and docosahexaenoic acid (DHA),
wherein the composition further comprises arachidonic acid, and
wherein the composition comprises a weight ratio of eicosapentaenoic acid to arachidonic acid of 1.5:1 or greater.

2. The method of claim 1, wherein the composition comprises at least 100 ppm L-carnitine.

3. The method of claim 1, wherein the composition comprises at least 200 ppm L-carnitine.

4. The method of claim 1, wherein the composition comprises 300 ppm L-carnitine.

5. The method of claim 1, wherein the composition comprises at least 0.10 weight % of one or both of EPA and DHA.

6. The method of claim 1, wherein the composition comprises at least 0.15 weight % of one or both of EPA and DHA.

7. The method of claim 1, wherein the composition comprises at least 0.30 weight % of one or both of EPA and DHA.

8. The method of claim 1, wherein the composition comprises at least 0.20 weight % fish oil.

9. The method of claim 1, wherein the composition comprises at least 0.50 weight % fish oil.

10. The method of claim 1, wherein the composition comprises at least 1.4 weight % fish oil.

11. The method of claim 1, wherein the composition comprises at least 0.10 weight % of one or more medium chain fatty acids.

12. The method of claim 1, wherein the composition comprises at least 0.15 weight % of one or more medium chain fatty acids.

13. The method of claim 1, wherein the composition comprises at least 1.4 weight % of one or more medium chain fatty acids.

14. The method of claim 11, wherein the one or more medium chain fatty acids are selected from capric acid, lauric acid, and myristic acid.

15. The method of claim 1, wherein the composition comprises one or more medium chain triglyceride oils.

16. The method of claim 15, wherein the composition comprises at least 1% of one or more medium chain triglyceride oils.

17. The method of claim 15, wherein the composition comprises at least 4% of one or more medium chain triglyceride oils.

18. The method of claim 15, wherein the composition comprises at least 8% of one or more medium chain triglyceride oils.

19. The method of claim 15, wherein the one or more medium chain triglyceride oils is coconut oil.

20. The method of claim 1, wherein the composition comprises one or both of coconut oil and corn oil.

21. The method of claim 1, wherein the composition comprises at least 2% linoleic acid (LA).

22. The method of claim 1, wherein the composition comprises at least 4% linoleic acid (LA).

23. The method of claim 1, wherein the composition comprises at least 1.5 weight % a-linolenic acid.

24. The method of claim 1, wherein the composition comprises a weight ratio of EPA to arachidonic acid of 2:1 or greater.

25. The method of claim 1, wherein the composition is a dog food and comprises a weight ratio of EPA to arachidonic acid of 3.8:1 or greater.

26. A method for the treatment or prophylaxis of kidney disease in a dog in need thereof comprising administering to the dog a composition comprising an effective amount of L-carnitine and both of eicosapentaenoic acid (EPA) and docosahexaenoic acid (DHA),
wherein the method for treatment or prophylaxis of kidney disease in the dog in need thereof further comprises reducing circulating arachidonic acid in the dog in need thereof,
wherein the composition further comprises arachidonic acid, and
wherein the composition comprises a weight ratio of eicosapentaenoic acid to arachidonic acid of 1.5:1 or greater.

* * * * *